US011497453B2

(12) United States Patent
Seo et al.

(10) Patent No.: US 11,497,453 B2
(45) Date of Patent: Nov. 15, 2022

(54) ELECTRONIC DEVICE AND METHOD FOR OBTAINING INFORMATION REGARDING BLOOD GLUCOSE OF USER

(71) Applicant: Samsung Electronics Co., Ltd., Gyeonggi-do (KR)

(72) Inventors: Hyejung Seo, Gyeonggi-do (KR); Minji Kim, Gyeonggi-do (KR); Jinho Kim, Gyeonggi-do (KR); Taehan Jeon, Gyeonggi-do (KR); Jeongmin Park, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 81 days.

(21) Appl. No.: 16/689,258

(22) Filed: Nov. 20, 2019

(65) Prior Publication Data
US 2020/0155081 A1 May 21, 2020

(30) Foreign Application Priority Data

Nov. 20, 2018 (KR) .................. 10-2018-0143463

(51) Int. Cl.
A61B 5/00 (2006.01)
A61B 5/145 (2006.01)
(Continued)

(52) U.S. Cl.
CPC ........ A61B 5/7278 (2013.01); A61B 5/14532 (2013.01); A61B 5/14552 (2013.01);
(Continued)

(58) Field of Classification Search
CPC .............. A61B 5/0059; A61B 5/02416; A61B 5/14532; A61B 5/14551; A61B 5/14552;
(Continued)

(56) References Cited

U.S. PATENT DOCUMENTS 5,459,317 A 10/1995 Small et al.
5,725,480 A * 3/1998 Oosta .................. A61B 5/0059
600/310
(Continued)

FOREIGN PATENT DOCUMENTS

CN 201481423 U 5/2010
EP 0 236 023 A3 9/1987
(Continued)

OTHER PUBLICATIONS

George Zionis, Aikaterini Dimou, Ioannis Bassukas, Dimitrios Galaris, Aygyrios Tsolakidis, Efthimios Kaxiras, "Melanin absorption spectroscopy: new method for noninvasive skin investigation and melanoma detection", Journal of Biomedical Optics 13(1), 014017 (Year: 2008).*
(Continued)

Primary Examiner — Allen Porter
Assistant Examiner — Abid A Mustansir
(74) Attorney, Agent, or Firm — Cha & Reiter, LLC

(57) ABSTRACT

An electronic device may include a housing and a PhotoPlethysmoGram (PPG) sensor disposed inside the housing. The PPG sensor may include a first Light Emitting Diode (LED) configured to generate light in a first wavelength band, a second LED configured to generate light in a second wavelength band, a third LED configured to generate light in a third wavelength band, a fourth LED configured to generate light in a fourth wavelength band, and a light receiving module including at least one photo diode. The electronic device may include a processor operatively coupled with the PPG sensor and a memory operatively coupled with the processor. The memory may include instructions that, when executed, cause the processor to measure optical densities of the light generated by the first
(Continued)

LED to the fourth LED, and calculate a blood glucose value based at least in part on the measured optical densities.

20 Claims, 19 Drawing Sheets

(51) Int. Cl.
*A61B 5/1455* (2006.01)
*A61B 5/024* (2006.01)

(52) U.S. Cl.
CPC .............. *A61B 5/443* (2013.01); *A61B 5/681* (2013.01); *A61B 5/742* (2013.01); *A61B 5/02433* (2013.01); *A61B 2562/0238* (2013.01); *A61B 2562/046* (2013.01)

(58) Field of Classification Search
CPC ....... A61B 5/443; A61B 5/681; A61B 5/7278; A61B 5/742; A61B 2562/0238; A61B 2562/046; A61B 5/02433
See application file for complete search history.

(56) References Cited

U.S. PATENT DOCUMENTS

| | | | |
|---|---|---|---|
| 6,847,835 B1* | 1/2005 | Yamanishi | A61B 5/0059 600/310 |
| 2013/0060098 A1 | 3/2013 | Thomsen et al. | |
| 2014/0276556 A1 | 9/2014 | Saint et al. | |
| 2017/0014035 A1 | 1/2017 | Newberry | |
| 2017/0071550 A1 | 3/2017 | Newberry | |
| 2017/0251963 A1* | 9/2017 | Hashimoto | A61B 5/14552 |
| 2017/0281027 A1 | 10/2017 | Altmejd et al. | |
| 2017/0337412 A1 | 11/2017 | Bhat et al. | |
| 2017/0337413 A1 | 11/2017 | Bhat et al. | |
| 2018/0125431 A1 | 5/2018 | Newberry | |
| 2018/0153520 A1 | 6/2018 | Esenaliev | |
| 2018/0214088 A1 | 8/2018 | Newberry | |
| 2018/0271431 A1 | 9/2018 | Lee et al. | |
| 2018/0303433 A1 | 10/2018 | Newberry | |
| 2020/0060585 A1* | 2/2020 | Harris | A61B 5/6824 |

FOREIGN PATENT DOCUMENTS

| | | |
|---|---|---|
| EP | 1491134 A1 | 12/2004 |
| EP | 1568310 A1 | 8/2005 |
| EP | 3189782 A1 | 7/2017 |
| JP | 2013-515528 A | 5/2013 |
| JP | 5726286 B2 | 5/2015 |
| KR | 10-1997-7001340 A | 3/1997 |
| KR | 10-2018-0106664 A | 10/2018 |
| KR | 10-2018-0106754 A | 10/2018 |
| WO | 2012/135079 A1 | 10/2012 |
| WO | 2017/115361 A1 | 7/2017 |
| WO | 2017/132404 A1 | 8/2017 |
| WO | 2018/064211 A1 | 4/2018 |
| WO | 2018169374 A1 | 9/2018 |

OTHER PUBLICATIONS

Lowndes; "Blood interference in fluorescence spectrum Experiment, analysis and comparison with intraoperative measurements on brain tumor"; Jul. 9, 2010; Linkoping University Institute of Technology.
Galeano, et al; "Analysis of Human Skin Hyper-Spectral Images by Non-negative Matrix Factorization"; 2011; Springer-Verlag Berlin Heidelberg.
Makpol, et al; "Comparable down-regulation of TYR, TYRP1 and TYRP2 genes and inhibition of melanogenesis by tyrostat, tocotrienol-rich fraction and tocopherol in human skin melanocytes improves skin pigmentation"; 2014; Societa Editrice Universo.
International Search Report dated Mar. 9, 2020.
European Search Report dated Feb. 8, 2022.
Indian Search Report dated Mar. 2, 2022.
European Search Report dated Oct. 7, 2021.

* cited by examiner

ELECTRONIC DEVICE AND METHOD FOR OBTAINING INFORMATION REGARDING BLOOD GLUCOSE OF USER

CROSS REFERENCE TO RELATED APPLICATION(S)

This application is based on and claims priority under 35 U.S.C. § 119(a) of a Korean patent application number 10-2018-0143463, filed on Nov. 20, 2018, in the Korean Intellectual Property Office, the disclosure of which is incorporated by reference herein in its entirety.

BACKGROUND

Field

Various embodiments described below generally relate to an electronic device for obtaining information regarding blood glucose, and a method thereof.

Description of Related Art

Chronic diseases require constantly monitoring and treatment by the user. Techniques are being developed for monitoring various aspects of the user relevant to the disease by using an electronic device such as a smartphone or a wearable device. Diabetes is one such chronic disease that requires constantly monitoring of the user's blood glucose levels. In order to measure the user's blood glucose, blood-gathering at one of the user's extremities is required by inserting a needle into user's skin. For example, when using an enzyme-based electrochemical analytical method, it is necessary to insert a micro-sized needle into an arm or abdomen to measure blood glucose in the user's capillaries.

SUMMARY

Non-invasive techniques for measuring blood glucose have been developed. But such techniques may require calibration based on invasive methods of glucose monitoring. For example, to calibrate, blood-gathering may need to be carried out multiple times (e.g., for each of various situations such as fasting/before-meal/after-meal or the like or for each designated period such as 5 minutes to 15 minutes). Therefore, even non-invasive methods of glucose monitoring may also lead to pain or extra cost.

Technical problems to be achieved in the disclosure are not limited to the technical problems mentioned above, and other technical problems not mentioned herein can be clearly understood by those skilled in the art to which the disclosure pertains from the following descriptions.

An electronic device according to an embodiment may include a housing and a PhotoPlethysmoGram (PPG) sensor disposed inside the housing. The PPG sensor may include a first Light Emitting Diode (LED) configured to generate light in a first wavelength band, a second LED configured to generate light in a second wavelength band, a third LED configured to generate light in a third wavelength band, a fourth LED configured to generate light in a fourth wavelength band, and a light receiving module including at least one photo diode, a processor operatively coupled with the PPG sensor, and a memory operatively coupled with the processor. The memory may include instructions that, when executed, cause the processor to measure optical densities of the light generated by the first LED to the fourth LED, and calculate a blood glucose value based at least in part on the measured optical densities.

An electronic device according to an embodiment includes a display, a sensor, a memory configured to store instructions, a plurality of LEDs configured to respectively emit a plurality of light beams having different wavelengths, and a processor operatively coupled with the display, the memory, and the sensor. The instructions, when executed, may cause the processor to identify a first input for measuring blood glucose from a user of the electronic device, acquire first information for measuring the blood glucose, based on the plurality of light beams emitted from the plurality of LEDs, in response to identifying the first input, calculate first blood glucose using the first information, obtain second information for measuring the blood glucose, based on the plurality of light beams emitted from the plurality of LEDs, in response to identifying a second input for measuring the blood glucose distinct from the first input, and calculate second blood glucose based at least in part on the first information and the second information, in response to the second input being identified within a designated time period after the first input.

Additional aspects will be set forth in part in the description which follows and, in part, will be apparent from the description, or may be learned by practice of the presented embodiments.

BRIEF DESCRIPTION OF THE DRAWINGS

Aspects, features, and advantages of certain embodiments of the present disclosure will be more apparent from the following description taken in conjunction with the accompanying drawings, in which.

DETAILED DESCRIPTION

According to one or more embodiments disclosed herein, an electronic device and a method thereof can more accurately acquire a concentration of blood glucose without blood-gathering causing pain to the user. The electronic device may achieve this by acquiring information necessary for measuring the concentration of blood glucose based on a non-invasive method.

Advantages of the instant disclosure are not limited to the aforementioned advantages, and other advantages not mentioned herein can be clearly understood by those skilled in the art to which the disclosure pertains from the following descriptions.

Hereinafter, one or more embodiments of the disclosure are described with reference to the accompanying drawings.

Figure 1:
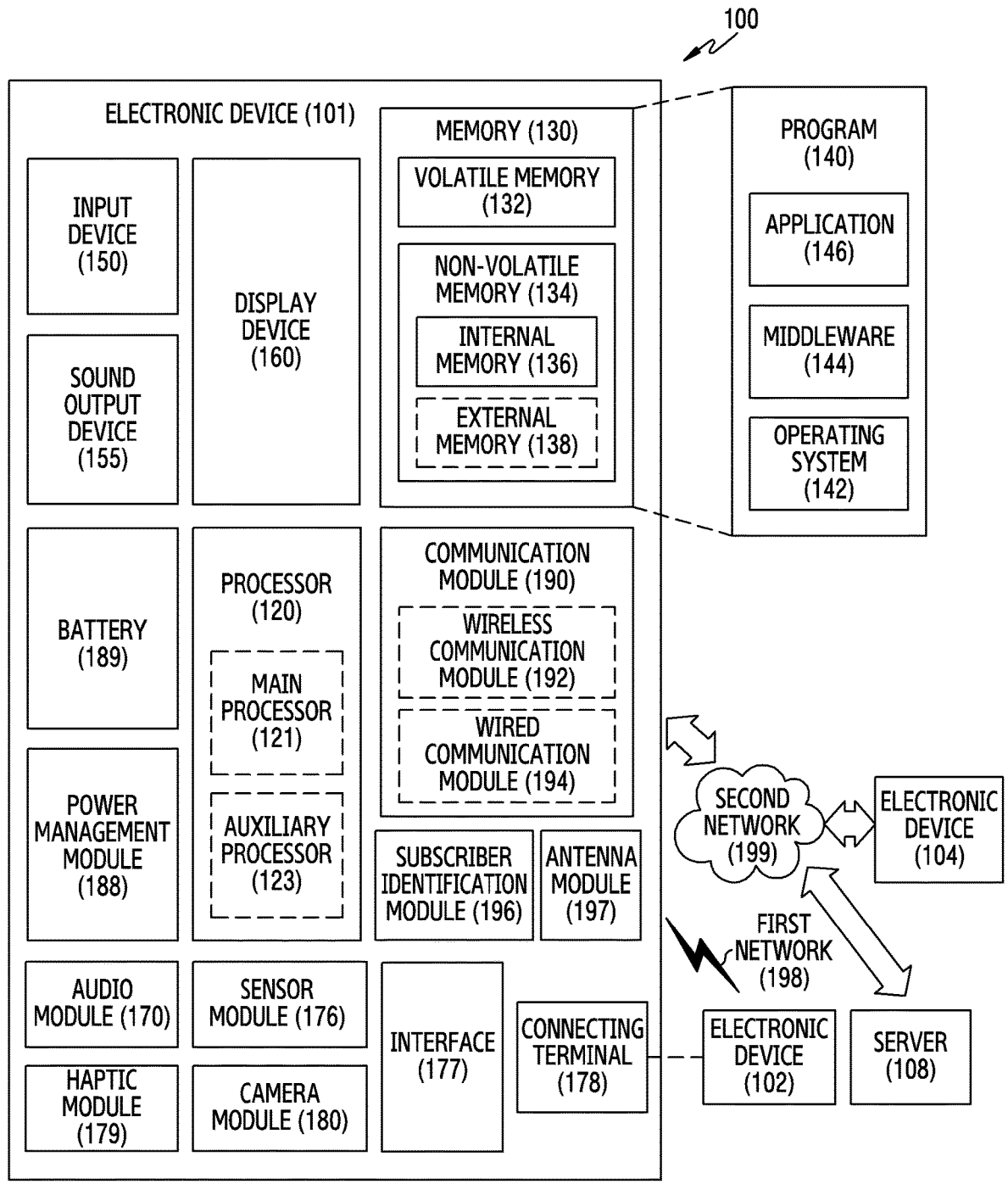
FIG. 1 is a block diagram of an electronic device in a network environment according to an embodiment.

FIG. 1 is a block diagram illustrating an electronic device (101) in a network environment (100) according to an embodiment. Referring to FIG. 1, the electronic device (101) in the network environment (100) may communicate with an electronic device (102) via a first network (198) (e.g., a short-range wireless communication network), or an electronic device (104) or a server (108) via a second network (199) (e.g., a long-range wireless communication network). According to an embodiment, the electronic device (101) may communicate with the electronic device (104) via the server (108). According to an embodiment, the electronic device (101) may include a processor (120), memory (130), an input device (150), a sound output device (155), a display device (160), an audio module (170), a sensor module (176), an interface (177), a haptic module (179), a camera module (180), a power management module (188), a battery (189), a communication module (190), a subscriber identification module (SIM) (196), or an antenna module (197). In some embodiments, at least one (e.g., the display device (160) or the camera module (180)) of the components may be omitted from the electronic device (101), or one or more other components may be added in the electronic device (101). In some embodiments, some of the components may be implemented as single integrated circuitry. For example, the sensor module (176) (e.g., a fingerprint sensor, an iris sensor, or an illuminance sensor) may be implemented as embedded in the display device (160) (e.g., a display).

The processor (120) may execute, for example, software (e.g., a program (140)) to control at least one other component (e.g., a hardware or software component) of the electronic device (101) coupled with the processor (120), and may perform various data processing or computation. According to one embodiment, as at least part of the data processing or computation, the processor (120) may load a command or data received from another component (e.g., the sensor module (176) or the communication module (190)) in volatile memory (132), process the command or the data stored in the volatile memory (132), and store resulting data in non-volatile memory (134). According to an embodiment, the processor (120) may include a main processor (121) (e.g., a central processing unit (CPU) or an application processor (AP)), and an auxiliary processor (123) (e.g., a graphics processing unit (GPU), an image signal processor (ISP), a sensor hub processor, or a communication processor (CP)) that is operable independently from, or in conjunction with, the main processor (121). Additionally or alternatively, the auxiliary processor (123) may be adapted to consume less power than the main processor (121), or to be specific to a specified function. The auxiliary processor (123) may be implemented as separate from, or as part of the main processor (121).

The auxiliary processor (123) may control at least some of functions or states related to at least one component (e.g., the display device (160), the sensor module (176), or the communication module (190)) among the components of the electronic device (101), instead of the main processor (121) while the main processor (121) is in an inactive (e.g., sleep) state, or together with the main processor (121) while the main processor (121) is in an active state (e.g., executing an application). According to an embodiment, the auxiliary processor (123) (e.g., an image signal processor or a communication processor) may be implemented as part of another component (e.g., the camera module (180) or the communication module (190)) functionally related to the auxiliary processor (123).

The memory (130) may store various data used by at least one component (e.g., the processor (120) or the sensor module (176)) of the electronic device (101). The various data may include, for example, software (e.g., the program (140)) and input data or output data for a command related thereto. The memory (130) may include the volatile memory (132) or the non-volatile memory (134).

The program (140) may be stored in the memory (130) as software, and may include, for example, an operating system (OS) (142), middleware (144), or an application (146).

The input device (150) may receive a command or data to be used by other component (e.g., the processor (120)) of the electronic device (101), from the outside (e.g., a user) of the electronic device (101). The input device (150) may include, for example, a microphone, a mouse, a keyboard, or a digital pen (e.g., a stylus pen).

The sound output device (155) may output sound signals to the outside of the electronic device (101). The sound output device (155) may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device (160) may visually provide information to the outside (e.g., a user) of the electronic device (101). The display device (160) may include, for example, a display, a hologram device, or a projector and control circuitry to control a corresponding one of the display, hologram device, and projector. According to an embodiment, the display device (160) may include touch circuitry adapted to detect a touch, or sensor circuitry (e.g., a pressure sensor) adapted to measure the intensity of force incurred by the touch.

The audio module (170) may convert a sound into an electrical signal and vice versa. According to an embodiment, the audio module (170) may obtain the sound via the input device (150), or output the sound via the sound output device (155) or a headphone of an external electronic device (e.g., an electronic device (102)) directly (e.g., wiredly) or wirelessly coupled with the electronic device (101).

The sensor module (176) may detect an operational state (e.g., power or temperature) of the electronic device (101) or an environmental state (e.g., a state of a user) external to the electronic device (101), and then generate an electrical signal or data value corresponding to the detected state. According to an embodiment, the sensor module (176) may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface (177) may support one or more specified protocols to be used for the electronic device (101) to be coupled with the external electronic device (e.g., the electronic device (102)) directly (e.g., wiredly) or wirelessly. According to an embodiment, the interface (177) may include, for example, a high definition multimedia interface (HDMI), a universal serial bus (USB) interface, a secure digital (SD) card interface, or an audio interface.

A connecting terminal (178) may include a connector via which the electronic device (101) may be physically connected with the external electronic device (e.g., the electronic device (102)). According to an embodiment, the connecting terminal (178) may include, for example, a HDMI connector, a USB connector, a SD card connector, or an audio connector (e.g., a headphone connector).

The haptic module (179) may convert an electrical signal into a mechanical stimulus (e.g., a vibration or a movement) or electrical stimulus which may be recognized by a user via his tactile sensation or kinesthetic sensation. According to an embodiment, the haptic module (179) may include, for example, a motor, a piezoelectric element, or an electric stimulator.

The camera module (180) may capture a still image or moving images. According to an embodiment, the camera module (180) may include one or more lenses, image sensors, image signal processors, or flashes.

The power management module (188) may manage power supplied to the electronic device (101). According to one embodiment, the power management module (188) may be implemented as at least part of, for example, a power management integrated circuit (PMIC).

The battery (189) may supply power to at least one component of the electronic device (101). According to an embodiment, the battery (189) may include, for example, a primary cell which is not rechargeable, a secondary cell which is rechargeable, or a fuel cell.

The communication module (190) may support establishing a direct (e.g., wired) communication channel or a wireless communication channel between the electronic device (101) and the external electronic device (e.g., the electronic device (102), the electronic device (104), or the server (108)) and performing communication via the established communication channel. The communication module (190) may include one or more communication processors that are operable independently from the processor (120) (e.g., the application processor (AP)) and supports a direct (e.g., wired) communication or a wireless communication. According to an embodiment, the communication module (190) may include a wireless communication module (192) (e.g., a cellular communication module, a short-range wireless communication module, or a global navigation satellite system (GNSS) communication module) or a wired communication module (194) (e.g., a local area network (LAN) communication module or a power line communication (PLC) module). A corresponding one of these communication modules may communicate with the external electronic device via the first network (198) (e.g., a short-range communication network, such as Bluetooth™, wireless-fidelity (Wi-Fi) direct, or infrared data association (IrDA)) or the second network (199) (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module (192) may identify and authenticate the electronic device (101) in a communication network, such as the first network (198) or the second network (199), using subscriber information (e.g., international mobile subscriber identity (IMSI)) stored in the subscriber identification module (196).

The antenna module (197) may transmit or receive a signal or power to or from the outside (e.g., the external electronic device) of the electronic device (101). According to an embodiment, the antenna module (197) may include a plurality of antennas. In such a case, at least one antenna appropriate for a communication scheme used in the communication network, such as the first network (198) or the second network (199), may be selected, for example, by the communication module (190) (e.g., the wireless communication module (192)) from the plurality of antennas. The signal or the power may then be transmitted or received between the communication module (190) and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device (101) and the external electronic device (104) via the server (108) coupled with the second network (199). Each of the electronic devices (102) and (104) may be a device of a same type as, or a different type, from the electronic device (101). According to an embodiment, all or some of operations to be executed at the electronic device (101) may be executed at one or more of the external electronic devices (102), (104), or (108). For example, if the electronic device (101) should perform a function or a service automatically, or in response to a request from a user or another device, the electronic device (101), instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device (101). The electronic device (101) may provide the outcome, with or without further processing of the outcome, as at least part of a reply to the request. To that end, a cloud computing, distributed computing, or client-server computing technology may be used, for example.

The electronic device according to certain embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that exemplary embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Certain embodiments as set forth herein may be implemented as software (e.g., the program (140)) including one or more instructions that are stored in a storage medium (e.g., internal memory (136) or external memory (138)) that is readable by a machine (e.g., the electronic device (101)). For example, a processor (e.g., the processor (120)) of the machine (e.g., the electronic device (101)) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium.

Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

Figure 2:
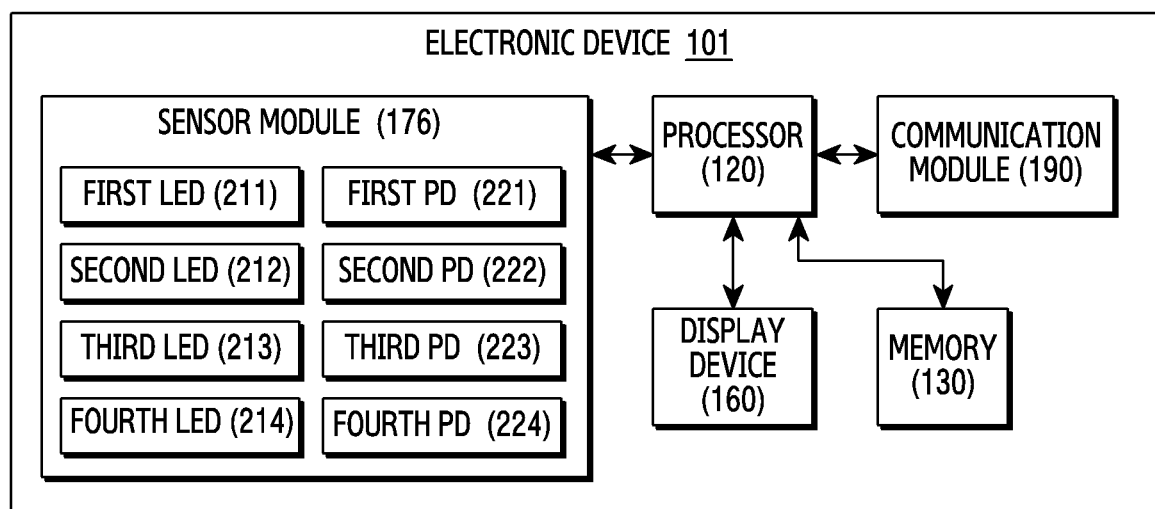
FIG. 2 is a block diagram of an electronic device 101 for measuring user's blood glucose according to an embodiment.

FIG. 2 is a block diagram of the electronic device 101 for measuring user's blood glucose according to an embodiment. The electronic device 101 may be a smartphone, a Personal Digital Assistant (PDA), a tablet Personal Computer (PC) such as a smart pad, a desktop PC, or a laptop PC. According to certain embodiments, the electronic device 101 may be an embedded PC which may be included as part of another electronic device, or may be a wearable device such as a smart watch.

Referring to FIG. 2, the electronic device 101 may include the processor 120, the memory 130, the display device 160, the sensor module 176, and the communication module 190. The processor 120, the memory 130, the display device 160, the sensor module 176, and the communication module 190 may be operatively coupled by an electrical interface such as a communication bus (not shown). The electronic device 101 according to this embodiment may be used to measure the user's blood glucose.

The processor 120 may compute data by using one or more instructions. The processor 120 may include at least one of an Arithmetic Logical Unit (ALU) which is used to compute the data, a Field Programmable Gate Array (FPGA), an Integrated Circuit (IC), and a Large Scale Integration (LSI). The processor 120 may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Certain of the functions and steps provided in the Figures may be implemented in hardware, software or a combination of both and may be performed in whole or in part within the programmed instructions of a computer. No claim element herein is to be construed under the provisions of 35 U.S.C. § 112(f), unless the element is expressly recited using the phrase "means for." In addition, an artisan understands and appreciates that a "processor" or "microprocessor" may be hardware in the claimed disclosure. Under the broadest reasonable interpretation, the appended claims are statutory subject matter in compliance with 35 U.S.C. § 101. The memory 130 operatively coupled with the processor 120 may store one or more instructions input to the processor 120 and data used by the processor 120. The processor 120 may identify one or more instructions stored in the memory 130, and may perform at least one of data generation, modification, or deletion based on the identified instructions.

The memory 130 may include at least one of a volatile memory such as a Static Random Access Memory (SRAM) or a Dynamic RAM (DRAM) and a non-volatile memory such as not only a Magnetoresistive RAM (MRAM), a Spin-Transfer Torque RAM (STT-MRAM), a Phase-Change RAM (PRAM), a Resistive RAM (RRAIVI), or a Ferroelectric RAM (FeRAM) but also an Embedded Multi Media Card (eMMC) or a Solid State Drive (SSD). One or more instructions and data associated with the memory 130 or the processor 120 may relate to the operation of measuring of the user's blood glucose by using a non-invasive method.

The display device 160 may be controlled by the processor 120 to provide a visual User Interface (UI) and other content to the user. The display device 160 may include a display which is at least partially viewable from the outside through a housing of the electronic device 101. The display may visually output information to the user and be an Organic Light Emitting Diode (OLED) display, a Liquid Crystal Display (LCD), or a Light Emitting Diode (LED) display. The UI which is output via the display may include a visual element or visual object related to the user's blood glucose.

The display 160 may include a Touch Screen Panel (TSP) (not shown) disposed above the display so that the user can more intuitively control the UI which is output by the display. The TSP may detect positions of touches or near-touches using resistive, capacitive, surface acoustic wave, and/or infrared technologies.

The communication module 190 may be coupled with the network 199 wirelessly based on at least one of Wireless-Fidelity (Wi-Fi) and Long Term Evolution (LTE). Alternatively, the communication module 190 may be coupled with the network 199 in a wired fashion based on at least one of Ethernet and a Local Area Network (LAN). The communication module 190 may include one or more hardware components (e.g., a communication circuit, an antenna element, etc.) for exchanging data generated by the processor 120 and data generated by the network 199. The communication module 190 may perform at least one of transmission and reception of a wired signal or wireless signal that includes information regarding the user's blood glucose.

The sensor module 176 may be disposed inside a housing (not shown) of the electronic device 101, and may include one or more hardware components for obtaining user's biometric information from a user's body part adjacent to the housing. The sensor module 176 may be a PhotoPlethysmoGram (PPG) sensor. The sensor module 176 may include one or more emitters at least partially exposed to the outside through the housing and one or more receivers corresponding to the one or more emitters. The emitter may be a light emitting module (e.g., a Light Emitting Diode (LED)). The receiver may be a light receiving module (e.g., a Photo Diode (PD)) which receives light corresponding to a wavelength of the LED. The user's biometric information obtained by the sensor module 176 may include one or more sensing values required to measure the user's blood glucose.

Referring to FIG. 2, the sensor module 176 may include four LEDs. Herein, "wavelength band of the LED" may refer to the wavelength band of the light output from the LED. When the sensor module 176 includes a plurality of LEDs, wavelength bands of each of the plurality of LEDs may not overlap with each other. At least one of the wavelength bands may be included in the Infrared (IR) wavelength band, i.e., a wavelength band greater than or equal to 780 nm. In addition, another wavelength band may be included in the visible light wavelength band, i.e., a wavelength band ranging from 380 nm to 750 nm.

In an embodiment of FIG. 2, the first LED 211 of the sensor module 176 may emit red light, the second LED 212 may emit green light, the third LED 213 may emit blue light, and the fourth LED 214 may emit infrared light. In an embodiment, the first wavelength band used by the first LED 211 may be between 645 nm and 700 nm. The second wavelength band used by the second LED 212 may be between 490 nm and 530 nm. The third wavelength band used by the third LED 213 may be between 430 nm and 480 nm. And the fourth wavelength band used by the fourth LED 214 may be greater than or equal to 780 nm.

Each of the first LED 211 to fourth LED 214 may be controlled by the processor 120. For example, each of the first LED 211 to fourth LED 214 may be activated and deactivated by the processor 120. The processor 120 may generate a control signal for controlling each of the first LED 211 to fourth LED 214 based on at least one of a designated intensity, a designated order, and a designated timing. The generated control signal may be transmitted to one of the LEDs, for example, via a communication bus (not shown). The designated intensity, order, and/or timing may be changed by the processor 120 or the user of the electronic device 101 to more accurately measure blood glucose.

The designated intensity may be associated with an intensity or amplitude of light emitted by each of the first LED 211 to fourth LED 214.

The designated order may be associated with an order in which each of the first LED 211 to fourth LED 214 receives the control signal or an order in which each of the first LED 211 to fourth LED 214 operates to emit light. The designated order may be configured such that at least some of the first LED 211 to fourth LED 214 operate simultaneously, or may be configured such that none of the first LED 211 to fourth LED 214 operates simultaneously.

The designated timing may be associated with, for example, a time at which an input for measuring blood glucose is received from the user while the LEDs are deactivated.

The number of LEDs included in the sensor module 176 is not limited to the embodiment of FIG. 2. In some embodiments, the sensor module 176 may include a tunable wavelength emitter capable of outputting light at various wavelengths in response to a control signal input from an external controller such as the processor 120. The processor 120 may control the tunable wavelength emitter to emit light of the first wavelength band to the fourth wavelength band.

When the sensor module 176 outputs light by using the aforementioned first LED 211 to fourth LED 214 or an emitter such as the tunable wavelength emitter, the output light may reach a user's body part adjacent to the housing. At least part of the output light may be reflected from the body part. At least one PD included in the sensor module 176 may be disposed inside the housing of the electronic device 101 to receive the reflection light reflected from the body part. A sensing value output from the sensor module 176 may include an Optical Density (OD) measured in the PD. When the PD is disposed inside the housing of the electronic device 101 to receive the reflection light reflected from the body part, the sensing value output from the sensor module 176 may correspond to the OD of the reflection light.

The wavelength band of the PD may imply a wavelength band in which the OD can change or a sensing value generated in the PD. The wavelength band of the PD may include all of the wavelength bands of the one or more LEDs included in the sensor module 176. When the sensor module 176 includes a plurality of LEDs or a plurality of PDs, the plurality of PDs may correspond to the respective wavelengths of the plurality of LEDs.

Referring to FIG. 2, the sensor module 176 may include four PDs. When the sensor module 176 includes a plurality of PDs, at least one of the wavelength bands of the plurality of PDs may be included in an Infrared (IR) wavelength band, i.e., a wavelength band greater than or equal to 780 nm. Among the other wavelength bands, another band may be included in the visible light wavelength band, i.e., a wavelength band ranging from 380 nm to 750 nm In an embodiment of FIG. 2, the first PD 221 to the fourth PD 224 may correspond to the first LED 211 to the fourth LED 214, and may be configured to respectively receive a plurality of reflection light beams reflected from at least part of the user's body. For example, the first PD 221 may receive red light, the second PD 222 may receive green light, the third PD 223 may receive blue light, and the fourth PD 224 may receive infrared light. In an embodiment, the wavelength band of the first PD 221 may include a first wavelength band (e.g., a wavelength band between 645 nm and 700 nm) used by the first LED 211. In an embodiment, the wavelength band of the second PD 222 may include a second wavelength band (e.g., a wavelength band between 490 nm and 530 nm) used by the second LED 212. In an embodiment, the wavelength band of the third PD 223 may include a third wavelength band (e.g., a wavelength band between 430 nm and 480 nm) used by the third LED 213. In an embodiment, the wavelength band of the fourth PD 224 may include a fourth wavelength band (e.g., a wavelength band greater than or equal to 780 nm) used by the fourth LED 214.

Each of the first PD 221 to fourth PD 224 may be controlled by the processor 120. For example, the processor 120 may generate a control signal for controlling each of the first PD 221 to fourth PD 224, based on a timing or order in which each of the first LED 211 to fourth LED 214 operates. The generated control signal may be transmitted to the first PD 221 to fourth PD 224, for example, via a communication bus (not shown). The PD which receives the control signal may be activated only for the time duration indicated by the received control signal. The activated PD may output a sensing value associated with an optical density of the reflection light received within the time duration. The output sensing value may be transmitted to the processor 120 or a controller (not shown) included in the sensor module 176.

The number of PDs included in the sensor module 176 is not limited to the embodiment of FIG. 2. In some embodiments, the sensor module 176 may include a tunable wavelength receiver capable of adjusting the wavelength band which can be received in response to a control signal input from an external controller such as the processor 120. In this embodiment, the sensor module 176 may include a PD capable of receiving a plurality of light beams having a plurality of wavelengths. The processor 120 may control the tunable wavelength receiver to receive light of the first wavelength band to the fourth wavelength band.

The processor 120 may calculate a blood glucose value of the user, based on the optical density of reflection light identified in one or more PDs included in the sensor module 176. The processor 120 may obtain the blood glucose value of the user based on one or more instructions stored in the memory. The processor 120 may use all of the first LED 211 to fourth LED 214 in order to identify factors having effect on the optical density of the reflection light in addition to the user's blood glucose. The factors having effect on the optical density of the reflection light in addition to the user's blood glucose may include, for example, at least one of a concentration of oxy-hemoglobin contained in user's blood, a concentration of deoxy-hemoglobin contained in the user's blood, a concentration of melanin contained in user's skin tissue, and a concentration of water contained in the user's skin tissue.

According to an embodiment, the processor 120 may identify each of factors having effect on the optical density of the reflection light in addition to the user's blood glucose, based on each of reflection light beams respectively received from the first PD 221 to the fourth PD 224. For example, the processor 120 may identify at least one of the oxy-hemoglobin concentration, the deoxy-hemoglobin concentration, and the melanin concentration, based on each of the optical densities. In an embodiment, at least one of the identified melanin concentration, oxy-hemoglobin concentration, and deoxy-hemoglobin concentration may be used for a plurality of blood glucose measurement requests input to the electronic device 101 within a designated time interval.

The processor 120 may calculate the blood glucose value by referring to at least one of the identified melanin concentration, the oxy-hemoglobin concentration, and the deoxy-hemoglobin concentration. For example, the processor 120 may remove or compensate for the effect of the identified oxy-hemoglobin concentration, deoxy-hemoglobin concentration, or melanin concentration on the optical densities, thereby extracting only an optical density change caused by the user's blood glucose. The processor 120 may obtain the user's blood glucose, based on the extracted optical density change caused by the user's blood glucose.

According to an embodiment, the LED included in the sensor module 176 may emit light of a wavelength band in which changes on the optical density of the reflection light caused by the concentration of water contained in the user's skin tissue is minimized. For example, the wavelength band between 645 nm and 700 nm, the wavelength band between 490 nm and 530 nm, and the wavelength band between 430 nm and 480 nm may be wavelength bands which are less affected by the concentration of water contained in the user's skin tissue. In an embodiment, the first LED 211 to third LED 213 may emit light included in the wavelength band between 645 nm and 700 nm, between 490 nm and 530 nm, and between 430 nm and 480 nm, respectively. In turn, the first PD 221 to the third PD 223 respectively corresponding to the first LED 211 to the third LED 213 may receive reflection light beams of the wavelength band less affected by the concentration of water contained in the user's skin tissue.

The electronic device 101 according to an embodiment may measure the user's blood glucose by using a non-invasive optical measurement technique. Light absorption characteristic of the user's skin tissue may be dependent on a state of the user's skin tissue. For example, hemoglobin or melanin contained in the skin tissue may have effect on the light absorption characteristic of the user's skin tissue in the visible and infrared wavelength bands.

As described above, the electronic device 101 according to an embodiment may identify at least one of the oxy-hemoglobin concentration, the deoxy-hemoglobin concentration, and the melanin concentration, thereby identifying the light absorption characteristic of the user's skin tissue. As described above, the electronic device 101 may identify the light absorption characteristic of the user's skin tissue, based on the optical sensors corresponding to the four wavelength bands of red light, green light, blue light, and infrared light. The identified light absorption characteristic may be identified as the user's individual characteristic. The electronic device 101 may correct the effect of the individual characteristic on the optical density of the reflection light, thereby more accurately identifying the effect of the user's blood glucose on the optical density of the reflection light.

The electronic device 101 may determine the user's blood glucose from the optical density of the reflection light, based on the identified light absorption characteristic. For example, the electronic device 101 may compensate for the effect of the oxy-hemoglobin, the deoxy-hemoglobin, or the melanin on the optical density of the reflection light. The electronic device 101 determines the blood glucose based on the light absorption characteristic of the user's skin tissue, thereby more accurately obtaining the user's blood glucose using the aforementioned non-invasive method.

Figure 3:
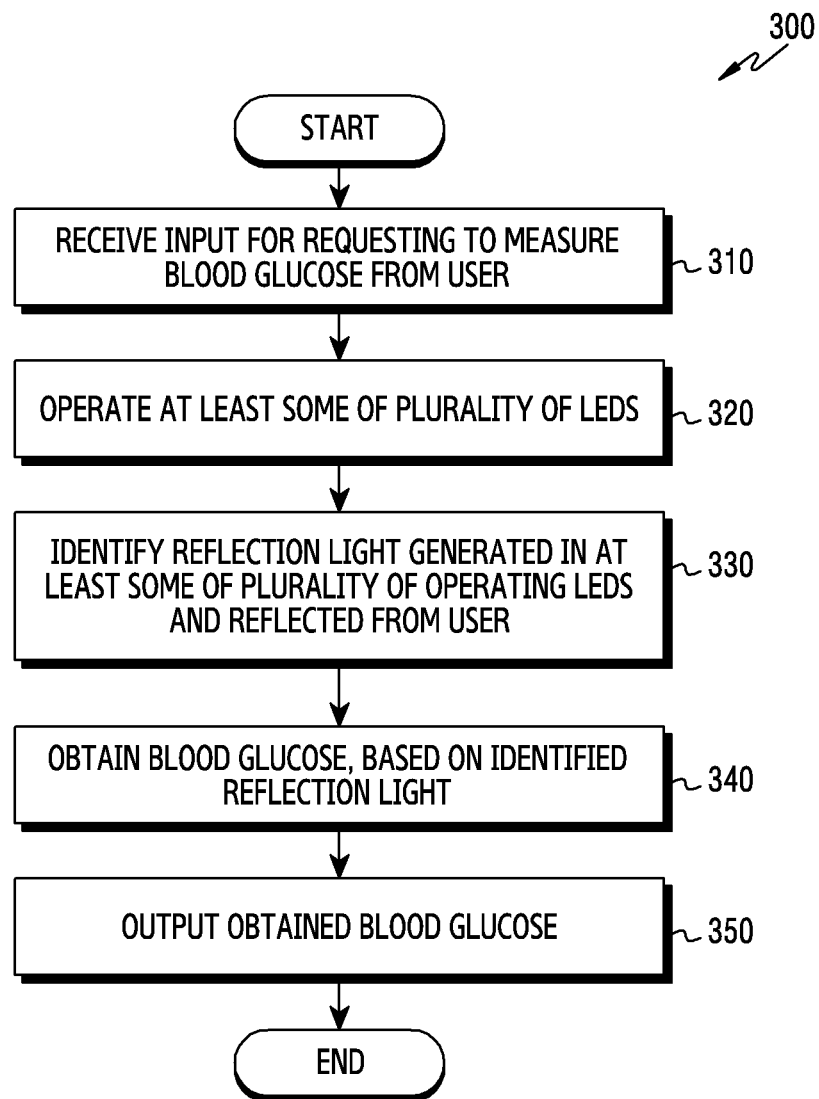
FIG. 3 is a flowchart illustrating an operation performed by an electronic device to measure user's blood glucose according to an embodiment.

FIG. 3 is a flowchart 300 illustrating an operation performed by an electronic device to measure user's blood glucose according to an embodiment. The electronic device of FIG. 3 may correspond to the electronic device 101 of FIG. 1 and FIG. 2. The operation of FIG. 3 may be performed by the electronic device 101 of the FIG. 1 and FIG. 2 or the processor 120 of FIG. 1 and FIG. 2. For example, the electronic device 101 may perform the operation of FIG. 3, based at least in part on a plurality of instructions stored in the memory 130 of FIG. 1 and FIG. 2.

Referring to FIG. 3, in operation 310, the electronic device according to an embodiment may receive a blood glucose measurement request from a user. For example, the user may execute an application related to the measurement of the blood glucose while the user is fasting. The user may perform an operation of selecting a visual element (e.g., a button displayed in a display) related to the measurement of the blood glucose, the visual element being included in the executed application. The operation of selecting the visual element may be done by clicking the visual element, by touching the visual element, and by using a dial or a button. In an embodiment, the user may push a button viewable on the display of the electronic device, thereby requesting the electronic device to measure the blood glucose. In an embodiment, the user may utter one or more words related to the measurement of blood glucose, thereby requesting the electronic device to measure the blood glucose. In an embodiment, the user may request the electronic device to initiate the measurement of the blood glucose at a designated timing such as 30 minutes after meal, i.e., while the user is not fasting.

In operation 320, the electronic device according to an embodiment may operate at least some of the plurality of LEDs, based on the input received from the user. For example, the electronic device may include the first LED 211 to fourth LED 214 of FIG. 2, and may operate at least some of the first LED 211 to fourth LED 214. In an embodiment in which the electronic device includes four LEDs, light having wavelength in a first wavelength band are emitted from the first LED, light having second wavelength band are emitted from the second LED, light having third wavelength band are emitted from the third LED, and light having fourth wavelength band are emitted from the fourth LED. The light of the four wavelengths may proceed towards the user's skin tissue simultaneously or sequentially based on a designated order. The first wavelength band to the fourth wavelength band may overlap with each other.

As at least some of the plurality of LEDs is operating, light corresponding to the operating LED may be emitted towards the user's skin tissue adjacent to the electronic device 101. In some embodiments, before the operation 320 is performed, the electronic device may identify whether the user is wearing the electronic device or whether the user's skin tissue is in proximity to the plurality of LEDs. If the user is not wearing the electronic device, the electronic device may request the user wear the electronic device. If the user's skin tissue is spaced apart by at least a designated distance from the plurality of LEDs, the electronic device may request the user move closer to the plurality of LEDs. For example, the electronic device may output a signal for requesting the user to move closer to be within the designated distance. The request to move closer may be in the form of a visual element such as text, image, and video output in the display, a voice signal output via a speaker, and/or a vibration signal output via a vibration motor.

Referring to FIG. 3, in operation 330, the electronic device according to an embodiment may identify the reflection light generated from at least some of the plurality of operating LEDs and reflected from the user. A sensor module including one or more LEDs and one or more PDs included in the electronic device may be exposed to the outside through part of the housing. In the case of a wearable electronic device for example, the housing may be in contact with at least part of the user's body. In the housing of the electronic device, one or more PDs may be disposed to receive the reflection light emitted from the LED operating in the operation 320 and reflected from at least part of the user's body (e.g., the user's skin tissue).

For example, the electronic device may include the first PD 211 to fourth PD 224 of FIG. 2. The electronic device may identify the optical density of the reflection light received through at least some of the first PD to the fourth PD. The identified optical density of the reflection light may differ from the optical density of the light emitted from at least some of the first LED to the fourth LED based on the operation 320. For example, the optical density of the reflection light may be more attenuated than the optical density of light that has not yet been reflected from the skin issue, due to a concentration of a plurality of materials contained in the skin tissue. The concentration of blood glucose contained in the skin tissue may also have effect on the optical density of the reflection light.

Human skin tissue may include epidermis and dermis. The plurality of materials contained in the skin tissue may be distributed differently in each of the epidermis and the dermis. For example, melanin may be mostly contained in the epidermis, and hemoglobin contained in the skin tissue may be mostly contained in the dermis. The hemoglobin may be classified into oxy-hemoglobin and deoxy-hemoglobin according to the number of bonded oxygen molecules. The concentration of hemoglobin may vary depending on the user's gender. The ratio between the oxy-hemoglobin and the deoxy-hemoglobin may vary depending on an oxygen bonding level (oxidation and reduction). The ratio may also vary depending on the user's physical condition. The amount or concentration of melanin, oxy-hemoglobin, and deoxy-hemoglobin contained in the skin tissue may have effect on the optical density of the reflection light.

Referring to FIG. 3, in operation 340, the electronic device according to an embodiment may obtain the blood glucose level based on the identified reflection light. The electronic device may obtain respective concentrations of the plurality of materials contained in the skin tissue, from the optical density of the identified reflection light. The plurality of materials may include at least one of the blood glucose, the melanin, the oxy-hemoglobin, and the deoxy-hemoglobin. For example, the electronic device may identify a plurality of reflection light beams having different wavelengths, and may compare optical densities of the plurality of identified reflection light beams to obtain the respective concentrations of the melanin, oxy-hemoglobin, and deoxy-hemoglobin contained in the skin tissue.

The electronic device may compensate for the effect of each of the melanin, the oxy-hemoglobin, and the deoxy-hemoglobin on the optical densities of the plurality of identified reflection light beams, based on the obtained respective concentrations of the melanin, oxy-hemoglobin, and deoxy-hemoglobin. Since the effect of each of the melanin, the oxy-hemoglobin, and the deoxy-hemoglobin on the optical densities of the plurality of identified reflection light beams is compensated for, the electronic device may identify the degree of attenuation of the reflection light according to the concentration of the blood glucose. The electronic device may obtain the user's blood glucose, based on the degree of attenuation of the reflection light according to the concentration of the blood glucose. This way, measurement for blood glucose may be made more accurate.

In an embodiment, the electronic device may measure the concentration of melanin in the user's skin tissue to correct the measurement error caused by the user's skin type. In an embodiment, the electronic device may measure the concentration of each of the oxy-hemoglobin and the deoxy-hemoglobin to correct the measurement error caused by the user's physical condition. In an embodiment, the electronic device may measure the concentration of each of the melanin, the oxy-hemoglobin, and the deoxy-hemoglobin in association with measuring the optical characteristic of the user's skin tissue to more accurately measure the user's blood glucose. The operation in which the electronic device obtains the user's blood glucose based on the operation 340 will be described in greater detail with reference to FIG. 5.

In some embodiments, the electronic device may store the measured concentration of each of the melanin, the oxy-hemoglobin, and the deoxy-hemoglobin for a designated time period or may share the concentration with an external electronic device.

Referring to FIG. 3, in operation 350, the electronic device according to an embodiment may output the blood glucose obtained in operation 340. The electronic device may provide the user with a change in the blood glucose over time, based on the blood glucose measured at various times. The electronic device may provide the user with information determined based on the obtained blood glucose, such as a diabetes diagnosing result, whether to inject a drug for adjusting the blood glucose, whether to restrict food intake, whether to perform a dietary regime, and/or whether to provide medical care.

The electronic device may output at least one of the obtained glucose, the change in the blood glucose, and the information to the user by using at least one of a display, a speaker, and a vibration motor. For example, the electronic device may output the obtained blood glucose as numerical text displayed in the display. For example, the electronic device may output a text message related to the blood glucose, such as "Visit nearby hospital,", "Blood glucose is within a risk range,", "Refrain from eating," "Insulin injection is recommended," etc.

Figure 4A:
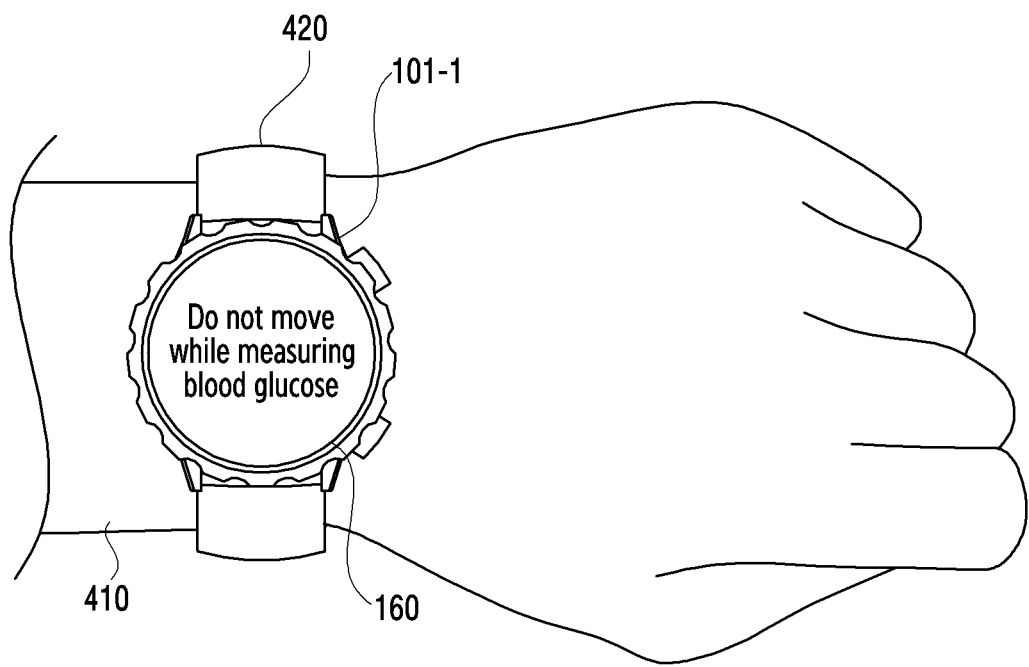
FIG. 4A is a view illustrating a User Interface (UI) provided to a user when an electronic device configured to be worn on a wrist performs the operation of FIG. 3 in some embodiments.
Figure 4B:
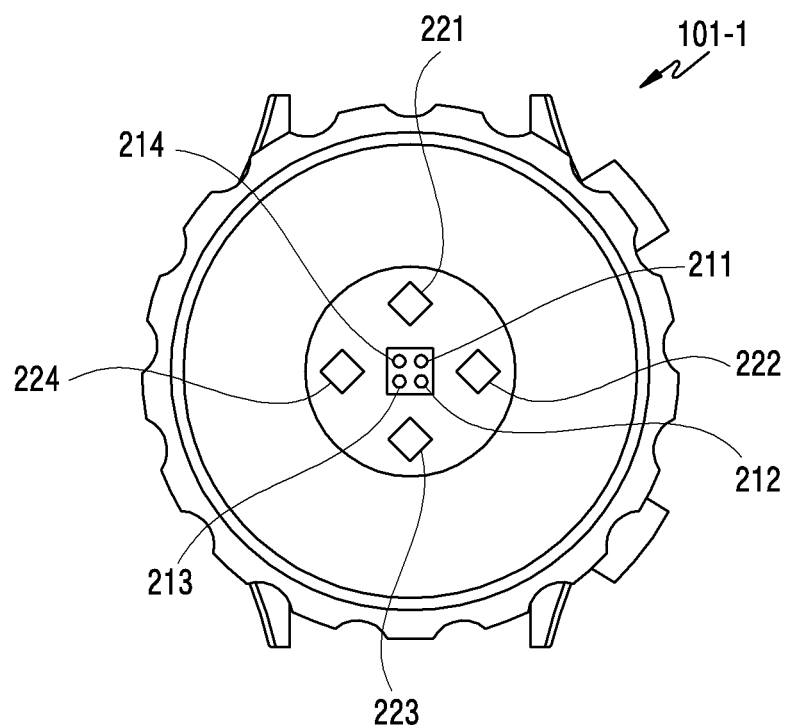
FIG. 4B is a view illustrating a UI provided to a user when an electronic device configured to be worn on a wrist performs the operation of FIG. 3 in some embodiments.
Figure 4C:
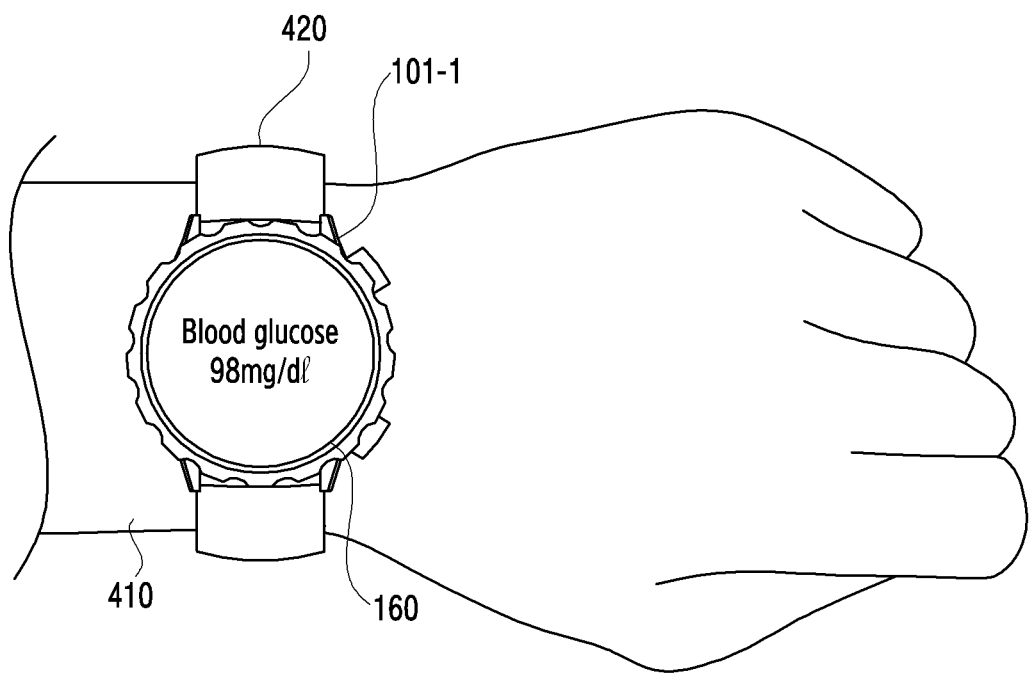
FIG. 4C is a view illustrating a UI provided to a user when an electronic device configured to be worn on a wrist performs the operation of FIG. 3 in some embodiments.

FIG. 4A to FIG. 4C are views illustrating an example of a User Interface (UI) provided to a user when an electronic device 101-1 configured to be worn on a wrist 410 performs the operation of FIG. 3 in an embodiment. The electronic device 101-1 of FIG. 4A to FIG. 4C may be associated with the electronic device 101 of FIG. 1 and FIG. 2. The housing of the electronic device 101-1 may have a similar shape as a wrist watch. The housing of the electronic device 101-1 may include a clip, hole, or bump to be coupled with a watch strap for fastening the electronic device 101-1 to the wrist 410. The watch strap 420 may be made of fabric, rubber, latex, and/or aluminum.

The display device 160 of the electronic device 101-1 may include a touch screen capable of detecting the user's touch or near-touch gestures. The electronic device 101-1 may include a dial and one or more buttons to receive the user's input. When the user requests to measure blood glucose by controlling at least one of the touch screen, the dial, and the button or by inputting a voice signal, the electronic device 101-1 may measure the blood glucose using a user's body part adjacent to the electronic device 101-1 (e.g. the wrist 410 shown in FIGS. 4A-4C).

Referring to FIG. 4A, an example of a User Interface (UI) is shown. The UI is output by the electronic device 101-1 via the display device 160 in response to a blood glucose measurement request received from the user. The electronic device 101-1 may output a message (e.g., "Blood glucose is being measured") indicating that the electronic device 101-1 is performing the measurement of the blood glucose. In order to more accurately measure the blood glucose, the electronic device 101-1 may output a message (e.g., "Do not move while measuring blood glucose.") for restricting the user's motion while measuring the blood glucose.

In an embodiment, the electronic device 101-1 may identify a distance between the wrist 410 and the electronic device 101-1, in response to the blood glucose measurement request received from the user. When the identified distance between the wrist 410 and the electronic device 101-1 exceeds a designated distance, the electronic device 101-1 may output a message (e.g., "Wear the electronic device 101-1 on the wrist 410") to prompt the user to move the electronic device 101-1 towards the wrist 410 to measure the blood glucose.

Referring to FIG. 4B, a face of a housing of the electronic device 101-1 adjacent to the wrist 410, for example, the bottom or rear face of the housing, is illustrated. The bottom face of the housing may on the opposite side of the face on which the display device 160 is disposed. When the user wears the electronic device 101-1 on the wrist 410, the front face of the housing in which the display device 160 is disposed may be facing out, and the rear face may be disposed towards skin tissue of the wrist 410.

A sensor module (e.g., the sensor module 176 of FIG. 2) of the electronic device 101-1 according to an embodiment may be disposed in the rear face of the electronic device 101-1. Referring to FIG. 4B, an example in which the first LED 211 to fourth LED 214 and first PD 211 to fourth PD 224 are disposed in the rear face of the electronic device 101-1 is shown. The first LED 211 to the fourth LED 214 may be disposed in a center of the rear face of the electronic device 101-1, and the first PD 221 to the fourth PD 224 may be disposed to be spaced apart by a designated distance from the center. The first LED 211 to the fourth LED 214 may respectively correspond to the first LED 211 to fourth LED 214 of FIG. 2. The first PD 221 to the fourth PD 224 may respectively correspond to the first PD 221 to fourth PD 224 of FIG. 2.

In response to the blood glucose measurement request received from the user, the electronic device 101-1 may operate the first LED 211 to the fourth LED 214. The first LED 211 to the fourth LED 214 may emit a plurality of light beams having different wavelengths towards the wrist 410. When the plurality of emitted light beams are reflected from the wrist 410, intensities of the plurality of light beams may be attenuated differently depending on concentrations of materials (e.g., blood glucose, water, melanin, oxy-hemoglobin, and deoxy-hemoglobin) contained in the skin tissue of the wrist 410 and the respective wavelengths of the plurality of light beams.

The electronic device 101-1 may measure optical densities of the reflection light beams reflected from the wrist 410 using the first PD 221 to the fourth PD 224. The electronic device 101-1 may calculate the user's blood glucose value based on the optical densities of the reflection light beams having the different wavelengths. In an embodiment, the electronic device 101-1 may apply designated weights to the respective optical densities measured at the first PD 221 to the fourth PD 224. The electronic device 101-1 may calculate the user's blood glucose value based on the weighted optical densities. When the electronic device 101-1 includes a plurality of PDs such as the first PD 221 to the fourth PD 224, a weight for a particular PD may be associated with the distance from the plurality of LEDs to that particular PD.

The electronic device 101-1 may provide the user with the calculated blood glucose value via the display device 160. Referring to FIG. 4C, an example of a UI which is output in the display device 160 by the electronic device 101-1 is shown. The electronic device 101-1 may output a blood glucose value calculated based on a designated unit (e.g., mg/dl). In an embodiment, the electronic device 101-1 may output the blood glucose value by using a visual element. In another embodiment, the electronic device 101-1 may provide the user with the blood glucose value by using the display device 160 and the speaker. For example, the electronic device 101-1 may control the speaker (not shown) to output a voice signal (e.g., "User's blood glucose is 98 mg/dl at the moment").

According to an embodiment, the electronic device 101-1 may provide the user with at least one of the calculated blood glucose value and information based on the blood glucose value (e.g., a result of diagnosing diabetes or whether to inject a drug for controlling blood glucose). In an embodiment, the electronic device 101-1 may provide the user with the user's skin characteristic (e.g., melanin concentration, oxy-hemoglobin concentration, and deoxy-hemoglobin concentration) determined based on at least one of optical densities of the reflection light beams measured by the first PD 221 to the fourth PD 224.

Figure 5:
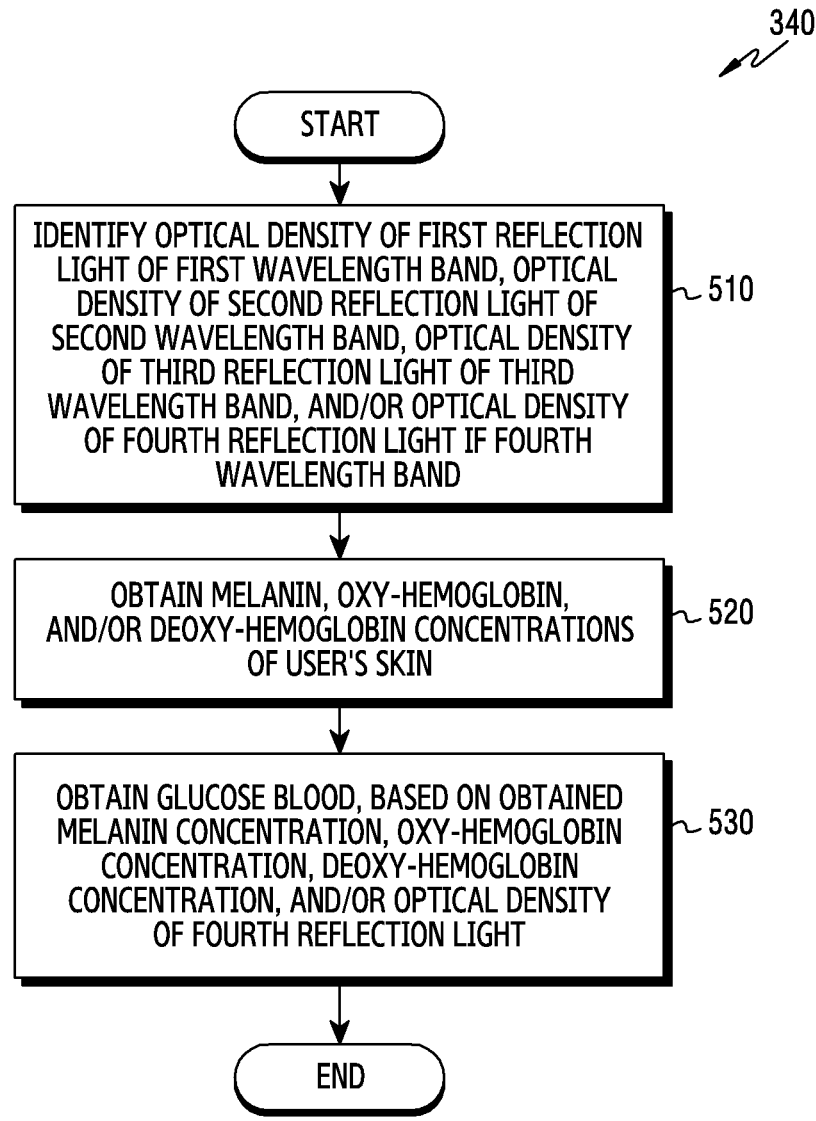
FIG. 5 is a flowchart for illustrating an operation in which an electronic device determines blood glucose based on reflection light beams obtained from at least some of a plurality of LEDs according to an embodiment.

FIG. 5 is a flowchart 340 for illustrating an operation in which an electronic device determines blood glucose based on reflection light beams obtained from at least some of a plurality of LEDs according to an embodiment. The electronic device of FIG. 5 may correspond to the electronic device 101 of FIG. 1 and FIG. 2. The operation of FIG. 5 may be performed by the electronic device 101 of FIG. 1 and FIG. 2 or the processor 120 of FIG. 1 and FIG. 2. The operations of FIG. 5 may be associated with the operation 340 of FIG. 3.

Referring to FIG. 5, in operation 510, the electronic device according to an embodiment may identify an optical density of first reflection light of a first wavelength band, an optical density of second reflection light of a second wavelength band, an optical density of third reflection light of a third wavelength band, and/or an optical density of fourth reflection light of a fourth wavelength band. The first wavelength band, the second wavelength band, the third wavelength band, and/or the fourth wavelength band may respectively correspond to wavelength bands between 645 nm and 700 nm, 490 nm and 530 nm, 430 nm and 480 nm, and greater than or equal to 780 nm.

Referring to FIG. 5, in operation 520, the electronic device according to an embodiment may obtain a melanin concentration, oxy-hemoglobin concentration, and deoxy-hemoglobin concentration of the user's skin. The obtained melanin concentration may indicate response by human skin tissue with respect to ultraviolet light. The obtained melanin concentration may be used to classify the human skin tissue into any one of a plurality of groups corresponding to the ultraviolet light response. For example, the obtained melanin concentration may be used to classify the human skin tissue into any one of designated 6 groups based on the Fitzpatric scale.

Hereinafter, the operation in which the electronic device obtains the melanin concentration, the oxy-hemoglobin concentration, and the deoxy-hemoglobin concentration based on a plurality of optical densities identified in operation 510 will be described in greater detail. The Optical Density (OD) of light passing through a medium may be attenuated based on Equation (1) related to the Beer-Lambert law. The electronic device may obtain a concentration of a material which absorbs or attenuates light from an optical density of reflection light based on Equation (1).

$$I = I_0 e^{-\varepsilon(\lambda)cL} \quad (1)$$

$$OD = \log\left(\frac{I_0}{I}\right) = \varepsilon cL$$

Referring to Equation (1), I may denote the intensity of the light after passing through a medium (e.g., air or user's skin tissue), and $I_0$ may denote the intensity of the light which is input to the medium. $\varepsilon(\lambda)$ may denote extinction coefficients. The extinction coefficient may have different values for different wavelength. c may denote the concentration of the medium. L may denote the transmission distance of the light passing through the medium. Referring to Equation (1), the OD may be associated with a ratio between intensities of light before and after passing through the medium.

Applying Equation (1), L may be associated with the distance between an LED and PD of the electronic device. The depth by which light is able to penetrate the skin issue may vary depending on the wavelength of the light and L (e.g., the depth may vary depending on whether the distance between the LED and the PD is 3 mm or 5 mm).

The light reflected from the skin tissue may vary by a sum of light absorption amounts by a plurality of materials affecting the optical characteristics of the skin tissue. The light absorption amount may vary depending on the wavelength of the light and the type of the material contained in the skin tissue. In an embodiment, concentrations of the materials affecting the light absorption of the skin tissue may be calculated based on the incident light and the reflection light of a plurality of wavelengths. For example, the electronic device may obtain concentrations of a plurality of materials affecting the optical characteristic of the skin tissue, based on Equation (2) and Equation (3).

$$\mu_a(\lambda) = \varepsilon_{Hb}(\lambda)C_{Hb} + \varepsilon_{Hb0}(\lambda)C_{Hb0} + \varepsilon_{Malanin}(\lambda)C_{Melanin} + \varepsilon_{abg}(\lambda)C_{abg} \quad (2)$$

$$\begin{cases} OD_{\lambda_1} = \left\{\varepsilon_{BG}^{\lambda_1}[BG] + \varepsilon_{Hb}^{\lambda_1}[Hb] + \varepsilon_{HB0}^{\lambda_1}[HB0] + \varepsilon_{Melanin}^{\lambda_1}[Malanin]\right\} \times L_1 \\ OD_{\lambda_2} = \left\{\varepsilon_{BG}^{\lambda_2}[BG] + \varepsilon_{Hb}^{\lambda_2}[Hb] + \varepsilon_{HB0}^{\lambda_2}[HB0] + \varepsilon_{Melanin}^{\lambda_2}[Malanin]\right\} \times L_2 \\ OD_{\lambda_3} = \left\{\varepsilon_{BG}^{\lambda_3}[BG] + \varepsilon_{Hb}^{\lambda_3}[Hb] + \varepsilon_{HB0}^{\lambda_3}[HB0] + \varepsilon_{Melanin}^{\lambda_3}[Malanin]\right\} \times L_3 \\ OD_{\lambda_4} = \left\{\varepsilon_{BG}^{\lambda_4}[BG] + \varepsilon_{Hb}^{\lambda_{34}}[Hb] + \varepsilon_{HB0}^{\lambda_4}[HB0] + \varepsilon_{Melanin}^{\lambda_4}[Malanin]\right\} \times L_4 \end{cases} \quad (3)$$

In Equation (2), $\mu_a(\lambda)$ may correspond to absorbance coefficient spectra. In Equation (2), Hb may denote deoxy-hemoglobin, Hbo may denote oxy-hemoglobin, and abg may denote absorbance blood glucose. In Equation (3), $\lambda_1$ to $\lambda_4$ may respectively correspond to the wavelengths of a plurality of light beams emitted respectively from the plurality of LEDs included in the electronic device. For example, $\lambda_1$ may denote a wavelength of 660 nm of red light emitted by a first LED (e.g., the first LED 211 of FIG. 2). $\lambda_2$ may denote a wavelength of 530 nm of green light emitted by a second LED (e.g., the second LED 212 of FIG. 2). $\lambda_3$ may denote a wavelength of 460 nm of blue light emitted by a third LED (e.g., the third LED 213 of FIG. 2). $\lambda_4$ may denote a wavelength of 950 nm of infrared light emitted by a fourth LED (e.g., the fourth LED 214 of FIG. 2).

In Equation (3), $L_1$ to $L_4$ may respectively denote distances between LEDs and PDs respectively corresponding to $\lambda_1$ and $\lambda_4$. For example, $L_1$ may denote the distance between an LED and PD associated with $\lambda_1$ (e.g., the distance between the first LED 211 and first PD 221 of FIG. 2). $L_2$ may denote the distance between an LED and PD associated with $\lambda_2$ (e.g., the distance between the second LED 212 and second PD 222 of FIG. 2). $L_3$ may denote the distance between an LED and PD associated with $\lambda_3$ (e.g., the distance between the third LED 213 and third PD 223 of FIG. 2). $L_4$ may denote the distance between an LED and PD associated with $\lambda_4$ (e.g., the distance between the fourth LED 214 and first PD 224 of FIG. 2). In Equation (3), [BG], [Hb], [HbO], and [Melanin] may respectively correspond to concentrations of blood glucose, deoxy-hemoglobin, oxy-hemoglobin, and melanin contained in the skin tissue.

The electronic device may obtain an extinction coefficient of at least one of blood glucose, oxy-hemoglobin, deoxy-hemoglobin, and melanin. The electronic device may obtain a concentration of at least one of blood glucose, oxy-hemoglobin, deoxy-hemoglobin, and melanin contained in the skin tissue from the obtained extinction coefficient.

Within the visible light wavelength band including $\lambda_1$ to $\lambda_3$, the light absorption amount from blood glucose may converge to or approximate '0,' or may be less than a designated reference value. In an embodiment, the electronic device may substitute for the parameter associated with the glucose of Equation (3) based on Equation (4).

$$\varepsilon_{BG}^{\lambda_1}[BG] \cong 0, \varepsilon_{BG}^{\lambda_2}[BG] \cong 0, \varepsilon_{BG}^{\lambda_3}[BG] \cong 0 \quad (4)$$

In an embodiment, the electronic device may obtain concentrations of a plurality of materials associated with the optical characteristic of the skin tissue, based on Equation (5) derived from Equation (3) and Equation (4) when only considering the light absorption amount within the visible light wavelength band.

$$\begin{cases} OD_{\lambda_1} = \left\{\varepsilon_{Hb}^{\lambda_1}[Hb] + \varepsilon_{HB0}^{\lambda_1}[HB0] + \varepsilon_{Melanin}^{\lambda_1}[Malanin]\right\} \times L_1 \\ OD_{\lambda_2} = \left\{\varepsilon_{Hb}^{\lambda_2}[Hb] + \varepsilon_{HB0}^{\lambda_2}[HB0] + \varepsilon_{Melanin}^{\lambda_2}[Malanin]\right\} \times L_2 \\ OD_{\lambda_3} = \left\{\varepsilon_{Hb}^{\lambda_3}[Hb] + \varepsilon_{HB0}^{\lambda_3}[HB0] + \varepsilon_{Melanin}^{\lambda_3}[Malanin]\right\} \times L_3 \end{cases} \quad (5)$$

Referring to Equation (5), the electronic device may obtain a concentration of each of oxy-hemoglobin, deoxy-hemoglobin, and melanin, based on a first-order linear equation having the concentrations of oxy-hemoglobin, deoxy-hemoglobin, and melanin as three variables. In an embodiment, in operation 520, the electronic device may obtain the concentration of each of oxy-hemoglobin, deoxy-hemoglobin, and melanin contained in the user's skin based on Equation (5).

Referring to FIG. 5, in operation 530, the electronic device according to an embodiment may obtain blood glucose based on the obtained concentrations of melanin, oxy-hemoglobin, and/or deoxy-hemoglobin. In an embodiment, the electronic device may obtain the user's blood glucose, based on the melanin, oxy-hemoglobin, and deoxy-hemoglobin concentrations obtained from Equation (5), and/or an optical density of infrared reflection light.

Glucose molecules contained in blood may absorb light having a wavelength of 950 nm which is in a near-Infrared (IR) wavelength band. In an embodiment, the electronic device may obtain the blood glucose concentration based on the light absorption amount of the near IR wavelength reflection light. When light having the wavelength of 950 nm is emitted towards the user's skin tissue, glucose and a plurality of other materials (e.g., oxy-hemoglobin, deoxy-hemoglobin, and melanin) may absorb the light.

In an embodiment, the electronic device may infer the degree in which the plurality of other materials absorbed the light having the wavelength of 950 nm. For example, the electronic device may identify the degree in which the plurality of other materials absorbed the light having the wavelength of 950 nm based on each of the oxy-hemoglobin, deoxy-hemoglobin, and melanin concentrations obtained in operation 520. From the initial light absorption amount of light having the wavelength of 950 nm, the electronic device may compensate for the light absorption amount caused by the plurality of other materials to calculate the light absorption amount caused by blood glucose.

For example, the electronic device may calculate the blood glucose concentration using Equation (6).

$$[BG] = \frac{1}{\varepsilon_{BG}^{\lambda_4}}\left\{\frac{OD^{\lambda_1}}{L_4}\right\} - \varepsilon_{Hb}^{\lambda_4}[Hb] - \varepsilon_{Hb0}^{\lambda_4}[Hb0] - \varepsilon_{Melanin}^{\lambda_4}[\text{Melanin}] \quad (6)$$

In Equation (6), $\lambda_4$ may correspond to the wavelength (e.g., 950 nm) included in an infrared wavelength band. In Equation (6), the concentration of each of oxy-hemoglobin, deoxy-hemoglobin, and melanin may be obtained based on the operation 520 or Equation (5).

FIG. 6A to FIG. 6D illustrate an example of a User Interface (UI) provided to a user by an electronic device 101-2 which is configured to measure blood glucose from a finger according to an embodiment. The electronic device 101-2 of FIG. 6A to FIG. 6D may be the electronic device 101 of FIG. 1 and FIG. 2. The electronic device 101-2 may be a smartphone, a smart pad, a PDA, or a tablet PC. At one face of the housing of the electronic device 101-2, at least part of the display device 160 may be viewable from the outside. The viewable portion of the display device 160 may be associated with a touch screen capable of detecting the user's touch gesture.

Figure 6A:
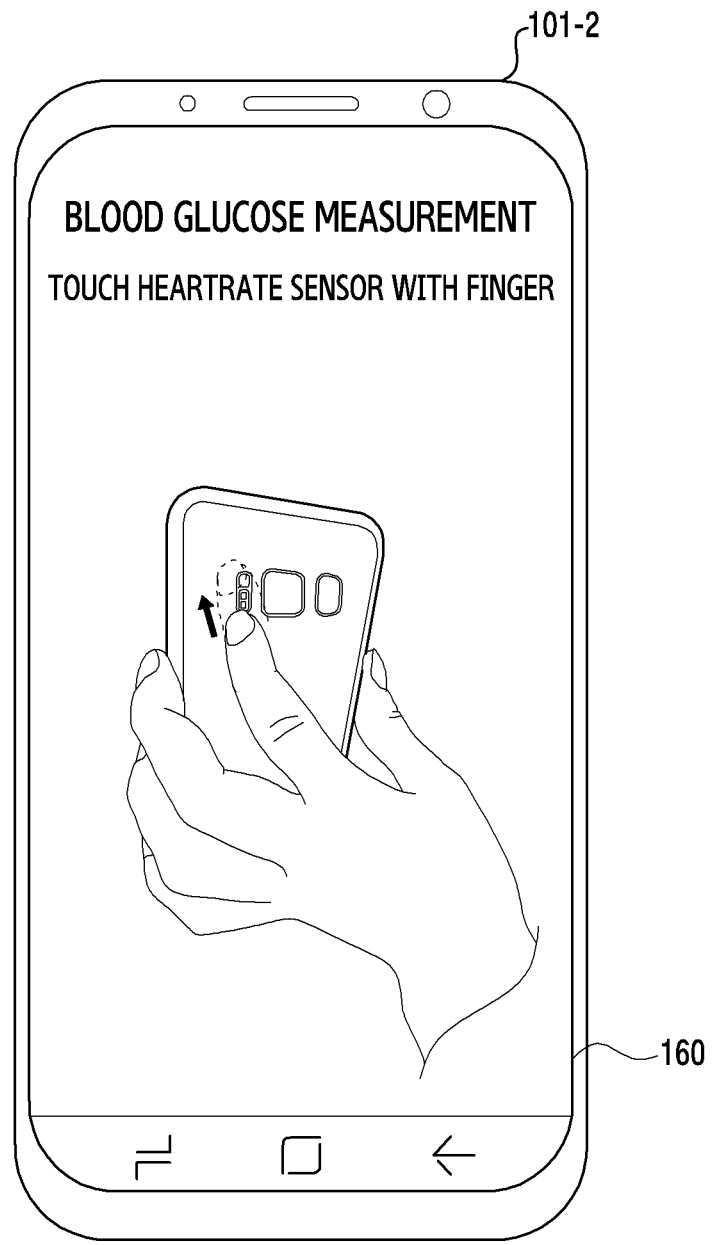
FIG. 6A illustrates an example of a UI provided to a user by an electronic device which is configured to measure blood glucose from a finger according to some embodiments.

Among a plurality of applications installed in the electronic device 101-2, a user may execute an application (e.g., a health application) related to measurement of blood glucose. Referring to FIG. 6A, an example of a UI which is output in the display device 160 by the electronic device 101-2 is shown. The UI is based on an application related to measurement of blood glucose and guides a user input related to measurement of blood glucose. The electronic device 101-2 may output at least one of text, image, video, and sound related to a user operation (e.g., an operation of touching a PPG sensor disposed to one face of the housing of the electronic device 101-2) required to measure blood glucose via the UI. In an embodiment, the electronic device 101-2 may guide the user to perform a designated action (e.g., the action of the user required to measure the blood glucose) using the display device 160 of the electronic device 101-2, a speaker, and/or a haptic actuator such as a vibration motor.

Figure 6B:
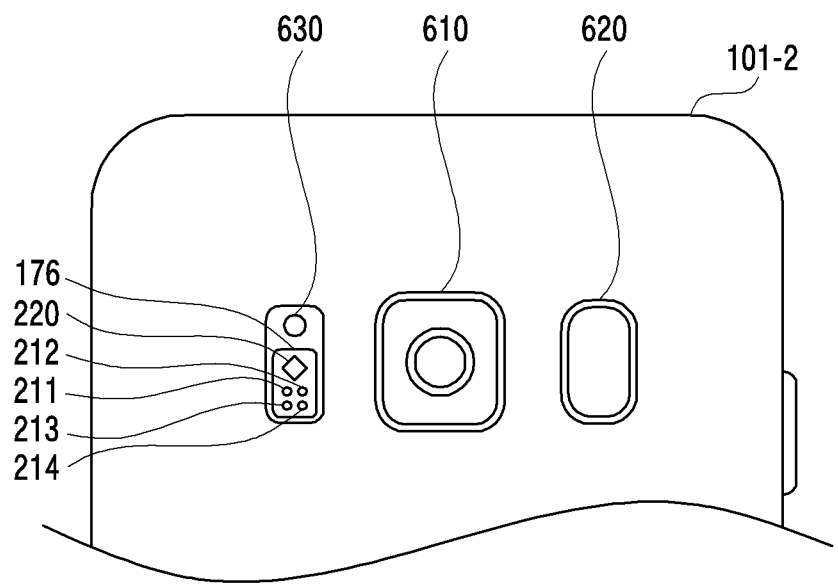
FIG. 6B illustrates an example of a UI provided to a user by an electronic device which is configured to measure blood glucose from a finger according to some embodiments.

Referring to FIG. 6B, a portion of another face distinct from the face of the housing of the electronic device 101-2 having the display device 160 is shown. The electronic device may include a sensor module 176 for measuring the user's heart rate or blood glucose. The sensor module of the electronic device 101-2 may be at least partially exposed to the outside through another face distinct from one face of the housing of the electronic device 101-2 having the display device 160. The sensor module 176 of FIG. 6B may correspond to the sensor module 176 of FIG. 2. In an embodiment, the sensor module 176 may include a plurality of LEDs (referring to FIG. 6B, the first LED 211, the second LED 212, the third LED 213, and the fourth LED 214). In an embodiment, the sensor module 176 may include at least one PD 220.

The other face on which the sensor module 176 is disposed may be a face opposite to the one face where the display is disposed. For example, the display device 160 may be disposed in a front face of the electronic device 101-2, and the sensor module 176 may be disposed in a rear face opposite to the front face. Referring to FIG. 6B, the rear face of the electronic device 101-2 may further include a rear camera 610, a fingerprint sensor 620, and/or a flash LED 630, together with the sensor module 176.

The user may touch the sensor module 176 of the electronic device 101-2 of FIG. 6B, based on the UI shown in FIG. 6A. The electronic device 101-2 may operate at least one of the plurality of LEDs included in the sensor module 176, based on detection of a user's touch on the sensor module 176. For example, the electronic device 101-2 may operate at least one of the first LED 211, second LED 212, third LED 213, and fourth LED 214 of FIG. 6B. The electronic device 101-2 may operate the PD 220 included in the sensor module 176 to obtain light reflected from the skin tissue after being emitted from at least one of the plurality of operating LEDs. The sensor module 176 may output data including an optical density of the obtained light.

Figure 6C:
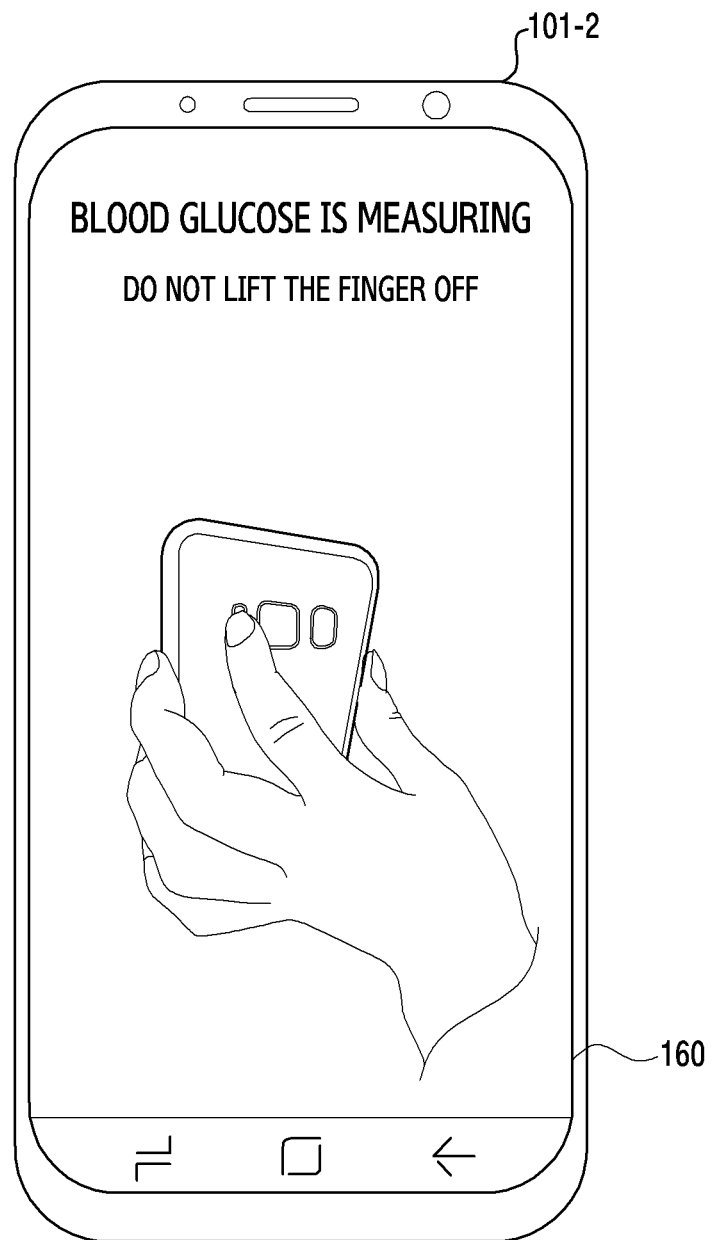
FIG. 6C illustrates an example of a UI provided to a user by an electronic device which is configured to measure blood glucose from a finger according to some embodiments.

Referring to FIG. 6C, an example of a UI provided by the electronic device 101-2 to a user in response to a touch of the sensor module 176 is shown. Based on detection a user's touch on the sensor module 176, the electronic device 101-2 may use the UI to provide the user with feedback associated with the touch of the sensor module 176. While the electronic device 101-2 obtains data associated with measurement of blood glucose from the sensor module 176, the electronic device 101-2 may provide the user with the feedback.

The electronic device 101-2 may request the user to touch the sensor module 176 until sufficient data to measure blood glucose is obtained from the sensor module 176. For example, the electronic device 101-2 may output to the display device 160 a message for maintaining the touch of the sensor module 176 (e.g., "Do not lift the finger off") until an optical density of reflection light is obtained by using the PD 220. In an embodiment, after detecting the user's touch on the sensor module 176, if the electronic device fails to obtain the optical density of the reflection light from the PD 220 for a designated time period or if at least any one of angle, pressure, and time period at which the user touches the sensor module 176 does not satisfy a designated criterion, the electronic device 101-2 may output the UI that includes a message indicating that blood glucose is not measured or a message for requesting to touch the sensor module 176 again or touch the sensor module 176 correctly.

In response to obtaining the optical density of the reflection light from the PD 220, the electronic device 101-2 may calculate the user's blood glucose. For example, the electronic device 101-2 may obtain the user's blood glucose based on at least some of the operations of FIG. 5 or Equation (5) and Equation (6). The electronic device 101-2 may obtain the user's blood glucose and information regarding the user's blood glucose based on weights associated with the structures of a plurality of PDs and a plurality of LEDs included in the sensor module 176.

Figure 6D:
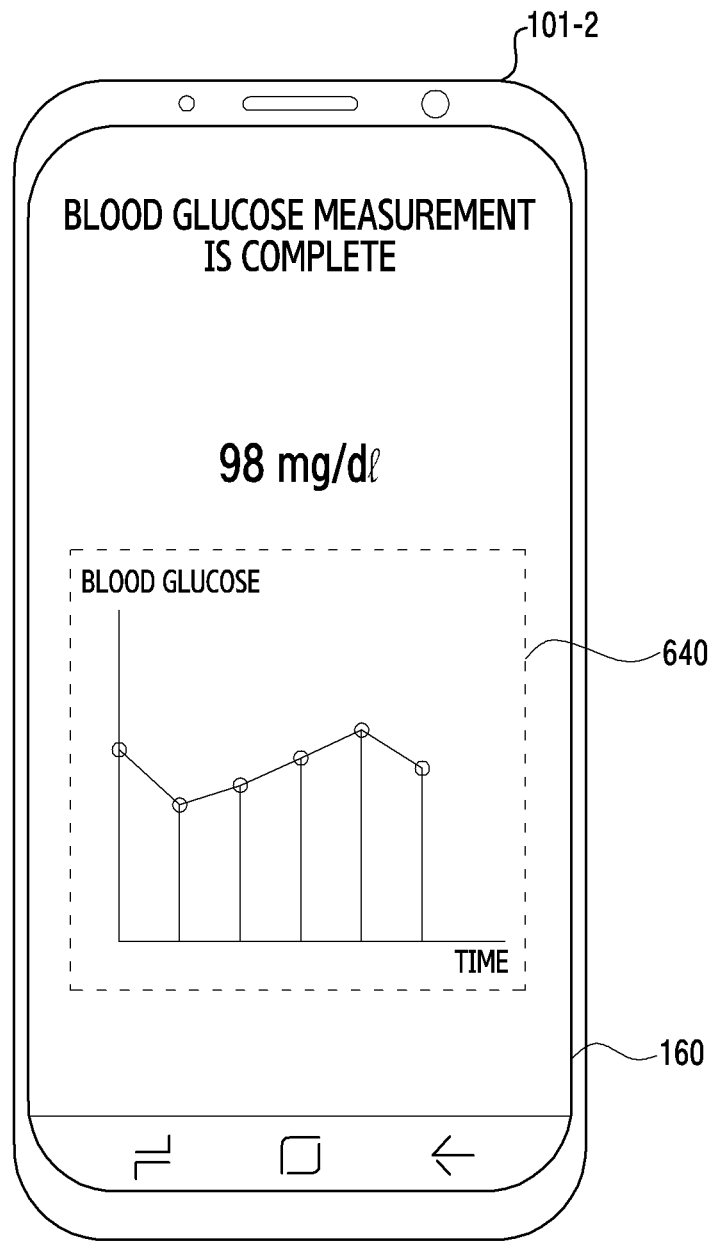
FIG. 6D illustrates an example of a UI provided to a user by an electronic device which is configured to measure blood glucose from a finger according to some embodiments.

The electronic device 101-2 may output the UI that includes the obtained user's blood glucose. Referring to FIG. 6D, an example of a UI that includes the result of the measured blood glucose is shown. The electronic device 101-2 may output the obtained blood glucose in voice, text, or numeric format. The electronic device 101-2 may output the obtained blood glucose in an image, animation, or graph format. In an embodiment of FIG. 6D, the electronic device 101-2 may output not only one recently measured blood glucose level but also a plurality of blood glucose levels measured within a designated time duration, and display the results as the graph 640.

Figure 7:
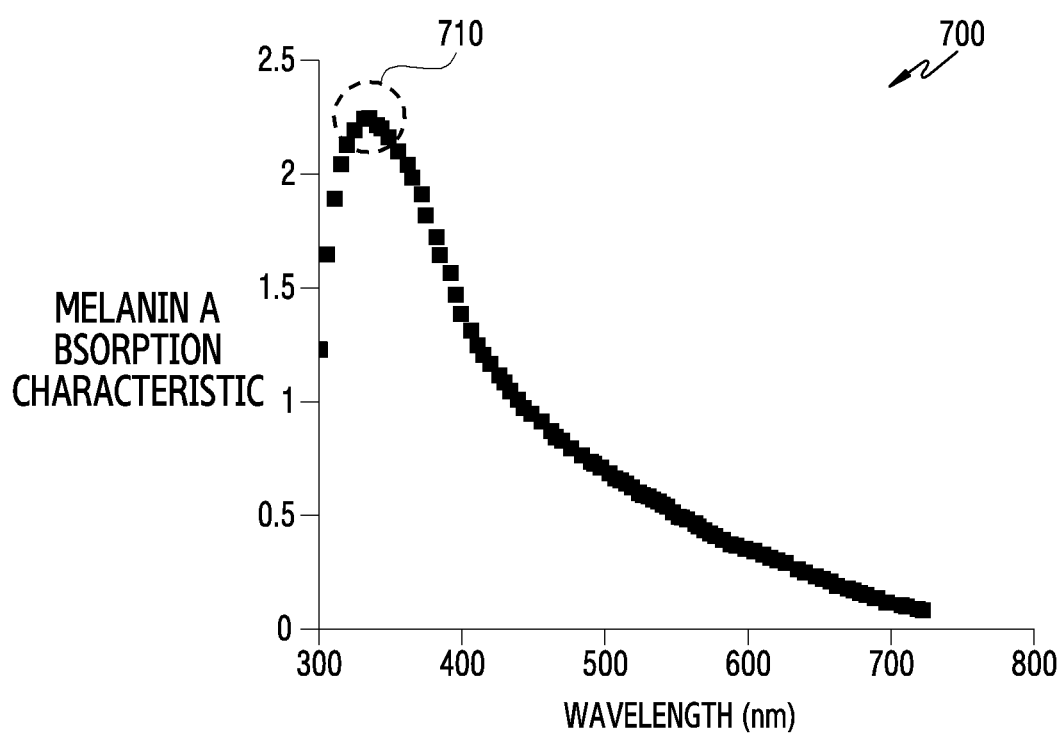
FIG. 7 is a graph illustrating an absorption spectrum of melanin measured for each wavelength of light emitted by an electronic device according to an embodiment.

FIG. 7 is a graph 700 illustrating an absorption spectrum of melanin measured for each wavelength of light emitted by an electronic device according to an embodiment. The electronic device of FIG. 7 may correspond to the electronic device 101 of FIG. 1 and FIG. 2.

In an embodiment, the electronic device may identify an optical characteristic of the skin tissue based on light of varying wavelengths. In an embodiment, the electronic device may obtain the optical density of reflection light reflected from the skin tissue for each wavelength. The electronic device may identify the optical characteristics of each of a plurality of materials contained in the skin tissue, such as an absorption characteristic based on a particular wavelength and a concentration. The plurality of materials may contain melanin.

FIG. 7 shows the degree at which melanin absorbs light ranges from an ultraviolet wavelength band (100 nm to 400 nm) to a visible light band (400 nm to 700 nm) to an infrared wavelength band greater than or equal to 700 nm. The melanin existing in epidermis of the skin tissue may absorb more light in the ultraviolet wavelength band. The degree at which the melanin absorbs light may increase as the wavelength of light gets closer to the ultraviolet wavelength band. Maximal absorption may occur at 710 between 300 nm and 400 nm.

In the visible light region, melanin may absorb relatively more light in the blue wavelength band. In an embodiment, the electronic device may obtain a concentration of melanin contained in the skin tissue, based on the absorption characteristic of the skin tissue within the blue wavelength band. The electronic device may obtain the concentration of melanin contained in the skin tissue, without interference caused by light absorption caused by water molecules contained in the skin tissue, based on the absorption characteristic of the skin tissue within the blue wavelength band.

Figure 8:
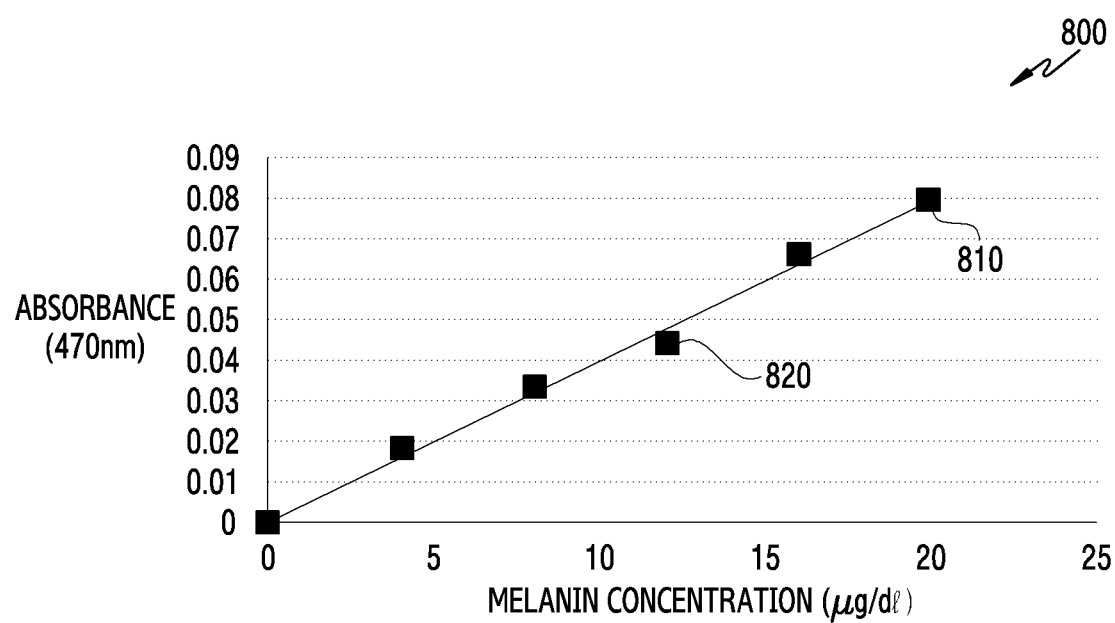
FIG. 8 is a graph illustrating absorbance as a function of melanin concentration of user's skin when an electronic device emits light having a wavelength of 470 nm according to an embodiment.

FIG. 8 is a graph 800 illustrating absorbance as a function of melanin concentration of user's skin when an electronic device emits light having a wavelength of 470 nm according to an embodiment. The electronic device of FIG. 8 may correspond to the electronic device 101 of FIG. 1 and FIG. 2.

In an embodiment, the electronic device may obtain the concentration of melanin contained in the skin tissue, based on the absorption characteristic of the skin tissue within the blue wavelength band. For example, the electronic device may emit light having a wavelength of 470 nm, which is included in the blue wavelength band, towards the user's skin tissue. In the embodiment described above, the electronic device may use the third LED 213 of FIG. 2 to output light having the wavelength of 470 nm. The electronic device may use the third PD 223 corresponding to the third LED 213 of FIG. 2 to receive light having the wavelength of 470 nm reflected from the user's skin tissue after being output from the third LED 213. The electronic device may obtain the concentration of melanin contained in the skin tissue, based on the optical density of received light having the wavelength of 470 m.

Referring to FIG. 8, the degree at which the light having the wavelength of 470 nm is absorbed into the skin tissue may be in proportion to the melanin concentration. In an embodiment, the electronic device may quantitatively calculate the concentration of melanin contained in the skin tissue, based on absorbance of light having the wavelength of 470 nm. For example, the absorbance of light having the wavelength of 470 nm of the skin tissue and the concentration of melanin in the skin tissue may have a linearly proportional relation. The electronic device may determine the concentration of melanin contained in the skin tissue, based on absorbance of light having the wavelength of 470 nm identified from reflection light having the wavelength of 470 nm.

For example, when the absorbance of light having the wavelength of 470 nm is 0.08, the electronic device may determine the melanin concentration of the skin tissue as 20 μg/dl, based on a point 810. In another example, when the absorbance of light having the wavelength of 470 nm ranges from 0.04 to 0.05, the electronic device may determine the melanin concentration of the skin tissue among values in the range of 12 μg/dl to 13 μg/dl, based on a point 820. As shown, the higher the absorbance of light having the 470 nm wavelength in the skin tissue, the higher the melanin concentration in the skin tissue, as determined by the electronic device.

In an embodiment, the electronic device may compensate for the effect of melanin in blood glucose measurements based on the melanin concentration calculated from the absorbance of light having the wavelength of 470 nm. In an embodiment, the electronic device may compensate for the change in the optical density of the reflection light caused by the melanin concentration to more accurately identify the change in the optical density of the reflection light caused by blood glucose concentration. The electronic device may calculate the blood glucose concentration based on the change in the optical density of the reflection light after compensating for melanin concentration.

Figure 9:
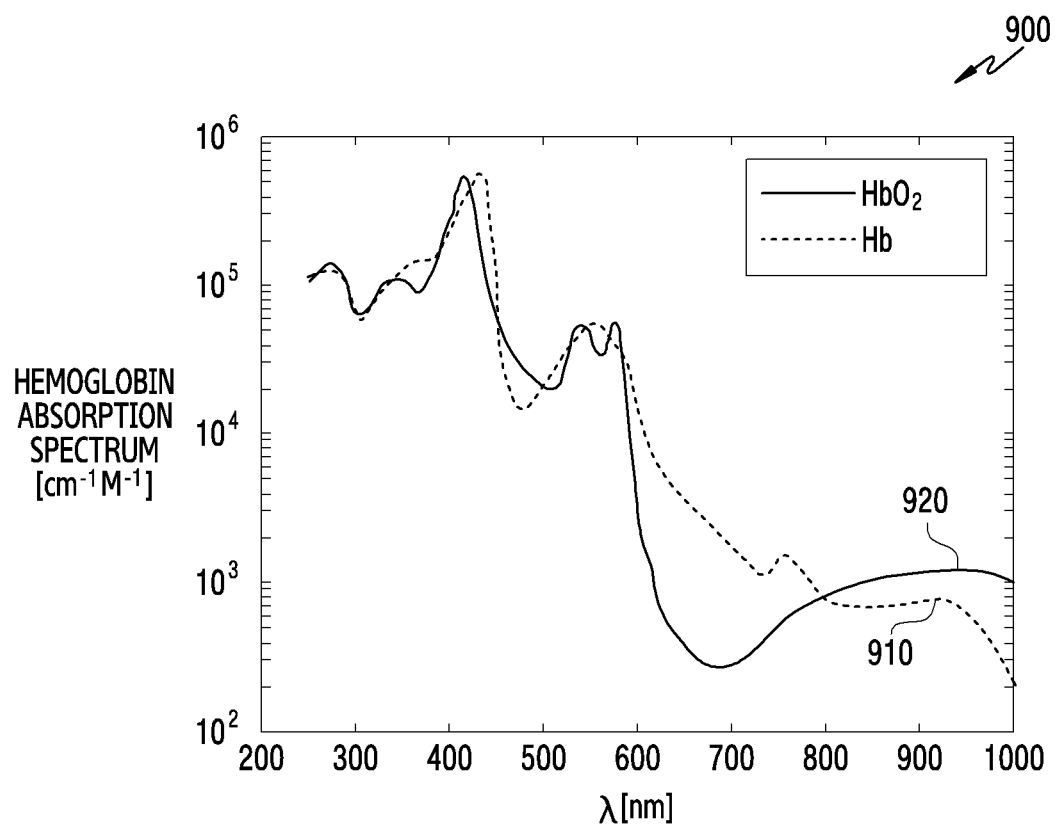
FIG. 9 is a graph illustrating an absorption spectrum of hemoglobin measured for various wavelength of light emitted by an electronic device according to an embodiment.

FIG. 9 is a graph 900 illustrating an absorption spectrum of hemoglobin measured for various wavelength of light emitted by an electronic device according to an embodiment. The electronic device of FIG. 9 may correspond to the electronic device 101 of FIG. 1 and FIG. 2.

In an embodiment, the electronic device may identify an absorption characteristic caused by each of a plurality of materials contained in skin tissue, such as absorption characteristic based on a particular wavelength and a concentration. The plurality of materials associated with the absorption characteristic identified by the electronic device may include at least one of oxy-hemoglobin and deoxy-hemoglobin.

FIG. 9 shows an absorption spectrum 910 for deoxy-hemoglobin contained in skin tissue and an absorption spectrum 920 for oxy-hemoglobin. Referring to the absorption spectrum 920 for oxy-hemoglobin, absorbance of oxy-hemoglobin may have peak values at wavelengths of about 400 nm, 500 nm, and 900 nm. Referring to the absorption spectrum 910 for deoxy-hemoglobin, absorbance of deoxy-hemoglobin may have peak values at wavelengths of about 400 nm, 500 nm, and 700 nm.

In an embodiment, the electronic device may obtain concentrations of oxy-hemoglobin and deoxy-hemoglobin contained in the skin tissue, based on the light absorption amount of light at wavelengths of 400 nm, 500 nm, and 600 nm. The electronic device may compensate for the attenuation caused by oxy-hemoglobin and deoxy-hemoglobin based on the obtained concentrations of oxy-hemoglobin and deoxy-hemoglobin. In an embodiment, the electronic device may compensate for a change in then optical density of the reflection light caused by each concentration of oxy-hemoglobin and deoxy-hemoglobin to better measure the change in the optical density of the reflection light caused by the blood glucose concentration. The electronic device may calculate the blood glucose concentration based on the change in the optical density of the reflection light caused by the blood glucose concentration.

In an embodiment, the electronic device may calculate concentrations of melanin, oxy-hemoglobin, and deoxy-hemoglobin contained in the skin tissue based on a plurality of light beams having at least three different wavelengths included in the visible light spectrum. The electronic device may calculate the concentrations of melanin, oxy-hemoglobin, and deoxy-hemoglobin contained in the skin tissue based at least in part on the operations of FIG. 5 to FIG. 9.

When the electronic device calculates the concentration of blood glucose contained in the skin tissue based on light having wavelengths in the infrared region, the calculated concentrations of melanin, oxy-hemoglobin, and deoxy-hemoglobin may be used. For example, the electronic device may compensate for how melanin, oxy-hemoglobin, and deoxy-hemoglobin affect the reflection light reflected from the skin tissue. The electronic device may compensate for a change in the optical density of the reflection light caused by melanin, oxy-hemoglobin and deoxy-hemoglobin to better measure the change in the optical density of the reflection light caused by the blood glucose concentration. The electronic device may calculate the blood glucose concentration based on the change in the optical density of the reflection light caused by the blood glucose concentration.

In response to another request from the user to measure blood glucose after a previous measurement for blood glucose is already done, the electronic device may use the previously calculated concentrations of melanin, oxy-hemoglobin, and/or deoxy-hemoglobin. For example, the electronic device may identify information regarding the melanin concentration of the user's skin issue, the oxy-hemoglobin concentration, and/or the deoxy-hemoglobin concentration of the user's blood. The identified information may be used by the electronic device to measure the user's blood glucose more rapidly in response to a subsequent request to measure blood glucose.

Figure 10:
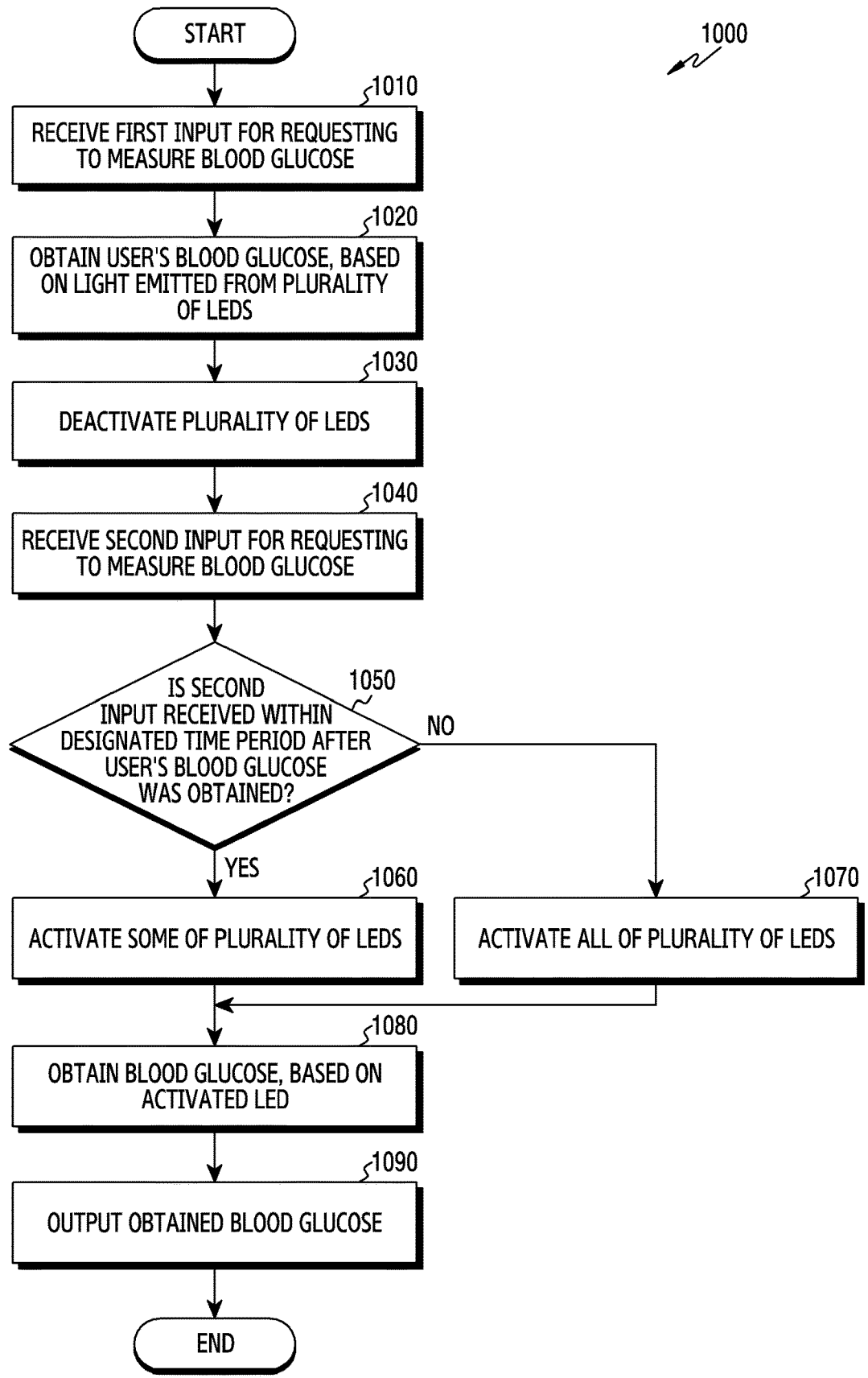
FIG. 10 is a flowchart illustrating an operation performed by an electronic device in response to a plurality of user inputs for measuring blood glucose according to an embodiment.

FIG. 10 is a flowchart 1000 illustrating an operation performed by an electronic device in response to a plurality of user inputs for measuring blood glucose according to an embodiment. The electronic device of FIG. 10 may correspond to the electronic device 101 of FIG. 1 and FIG. 2. That is, the operation of FIG. 10 may be performed by the electronic device 101 of FIG. 1 and FIG. 2 or the processor 120 of FIG. 1 and FIG. 2.

Referring to FIG. 10, in operation 1010, the electronic device according to an embodiment may receive a first input for requesting measurement of blood glucose from a user. The first input may be an input for measuring blood glucose while the user is fasting. Alternatively, the first input may be an input for measuring after-meal blood glucose after a designated period (e.g., 30 minutes). The first input may be an input requested by another user (e.g., a doctor associated with the user) distinct from the user of the electronic device.

Referring to FIG. 10, in operation 1020, the electronic device according to an embodiment may obtain user's blood glucose based on light emitted from a plurality of LEDs. The operation 1020 may be performed based at least in part on the operations of FIG. 3 or FIG. 5. In an embodiment, the electronic device may operate the plurality of LEDs. The plurality of LEDs may include three LEDs for outputting light corresponding to three visible wavelength bands not overlapping with each other. The three wavelength bands may include a first wavelength band of between 645 nm and 700 nm, a second wavelength band of between 490 nm and 530 nm, and a third wavelength band of between 430 nm and 480 nm. The plurality of LEDs may further include an LED for outputting light in the infrared wavelength band distinct from the visible light wavelength bands.

The electronic device may obtain a melanin concentration of user's skin tissue, a concentration of oxy-hemoglobin contained in user's blood, and a concentration of deoxy-hemoglobin contained in the blood, based on the plurality of visible light beams emitted from the three LEDs. The electronic device may identify these concentrations based on optical densities of a plurality of reflection light beams respectively corresponding to the plurality of emitted light beams and reflected from the user's skin tissue.

For example, the electronic device may calculate at least one of the melanin concentration, the oxy-hemoglobin concentration, and the deoxy-hemoglobin concentration, based on the operation of FIG. 5 and at least one of Equation (3) to Equation (5). The electronic device may identify the optical density corresponding to the infrared light reflected from the user's skin tissue. The electronic device may obtain a concentration of blood glucose from the optical density of the reflection infrared light and the calculated melanin, oxy-hemoglobin, or deoxy-hemoglobin concentrations.

In operation 1020, the electronic device may obtain first information corresponding to the received first input. The first information may include information on the melanin concentration, the oxy-hemoglobin concentration, and/or the deoxy-hemoglobin concentration. The first information may be based on the plurality of light beams emitted from the plurality of LEDs. The first information may include information on the user's blood glucose. The electronic device may provide the user with at least part of the obtained first information. The electronic device may store at least part of the obtained first information in a memory (e.g., the memory 130 of FIG. 2). The electronic device may transmit at least part of the obtained first information to an external electronic device. The external electronic device may be associated with a server which provides the user with a health-related service.

Referring to FIG. 10, in operation 1030, the electronic device according to an embodiment may deactivate the plurality of LEDs. In an embodiment, deactivation of an LED may mean that the LED is not operating before the user provides the electronic device 101 with the input for measuring the blood glucose. In an embodiment, the deactivation of the LED may mean a state where the processor 120 is not generating a control signal associated with the deactivated LED, in response to receiving the input for measuring the blood glucose from the user. In an embodiment, the deactivation of the LED may mean a state where power supplied to the LED is cut off and thus the LED is not operating, before the processor 120 generates the control signal associated with the deactivated LED, in response to receiving the input for measuring the blood glucose from the user. The plurality of LEDs may be deactivated after the first information is obtained. After being deactivated, at least one of the plurality of LEDs may maintain an inactive state for a designated time period. For example, the electronic device may deactivate three LEDs corresponding to the visible light wavelength band. Within the designated time period, the deactivated LEDs may not be reactivated.

After the plurality of LEDs are deactivated, in operation 1040, the electronic device according to an embodiment may receive a second input for requesting to measure blood glucose from the user. The electronic device may receive an input for requesting to acquire second information regarding the blood glucose from the user. The second input may be an input distinct from the first input. The second information may be information distinct from the first information.

In response to receiving the second input, in operation 1050, the electronic device according to an embodiment may determine whether the second input is received within a designated time period after the user's blood glucose was first obtained in response to the first input. For example, in response to receiving the second input, the electronic device may determine whether the designated time period has elapsed from when the blood glucose measurement was first obtained from the first information in operation 1020. In response to receiving the second input, the electronic device may activate some of the plurality of LEDs, based on when the first information was obtained and when the second input was received. Which particular LEDs should be activated may depend from the difference between when the first information was obtained and when the second input was received.

In response to the second input being received after the designated time period has elapsed from when the user's blood glucose was first obtained, in operation 1070, the electronic device according to an embodiment may activate all of the plurality of LEDs. For example, when the second input is received after the designated time period has elapsed from when the blood glucose was first obtained from the first information in operation 1020, the electronic device may activate all of the plurality of LEDs. In an embodiment, the electronic device may perform the operation of measuring the user's blood glucose in response to the second input, similarly when it measured the user's blood glucose in response to the first input.

In response to the second input received within the designated time period after the user's blood glucose was first obtained, in operation 1060, the electronic device according to an embodiment may activate some of the plurality of LEDs. For example, when the second input is received after the designated time period has elapsed from when the blood glucose was first obtained from the first information in operation 1020, the electronic device may activate some of the plurality of LEDs.

In operation 1060, the electronic device may activate the infrared LED while maintaining the other visible-spectrum LEDs in their deactivated states. In this embodiment, the electronic device may emit infrared light without emitting visible light to the user's skin tissue, in response to the second input. Thus, the type and number of LEDs to be activated in response to the second input may vary depending on the timing of the first and second inputs.

Referring to FIG. 10, in operation 1080, the electronic device according to an embodiment may obtain blood glucose based on the activated LED. When all of the plurality of LEDs are activated based on the operation 1070, the electronic device may obtain blood glucose from optical densities of a plurality of reflection light beams obtained by using all of the plurality of LEDs. The operation in which the electronic device obtains the blood glucose by using all of the plurality of LEDs may be performed similarly to the operation 1020.

When some of the plurality of LEDs are activated based on the operation 1060, the electronic device may obtain the second information corresponding to the second input and regarding blood glucose, based light beams emitted from the activated LEDs. The second information may also be based at least in part on the first information obtained in the operation 1020. For example, the electronic device may calculate user's blood glucose associated with the second input, based on at least one of melanin, oxy-hemoglobin, and deoxy-hemoglobin concentrations measured in response to the first input. For example, in response to the second input being received within a designated time period after the first information was obtained, the electronic device may obtain the second information based at least on the melanin, oxy-hemoglobin, and deoxy-hemoglobin obtained in response to the first input.

Referring to FIG. 10, in operation 1090, the electronic device according to an embodiment may output the obtained blood glucose to the user. The electronic device may display the second information corresponding to the second input, where the second information includes a value associated with the blood glucose. The second information may be output together with the first information. The operation in which the electronic device stores at least part of the obtained second information or transmits it to an external electronic device may be performed similarly as described in connection with the operation 1020.

Referring to operations 1050 and 1060, the electronic device according to an embodiment may identify information obtained from the user before a user input (e.g., second input) for requesting to calculate a blood glucose is received. The information may include at least one of the melanin concentration, the oxy-hemoglobin concentration, and the deoxy-hemoglobin concentration. When the information was previously obtained, the electronic device may limit the operation of one or more LEDs (e.g., the first LED 211 to third LED 213 of FIG. 2) that emit visible light. Accordingly, the electronic device may operate only the LED (e.g., the fourth LED 214 of FIG. 2) that emits infrared light.

Figure 11:
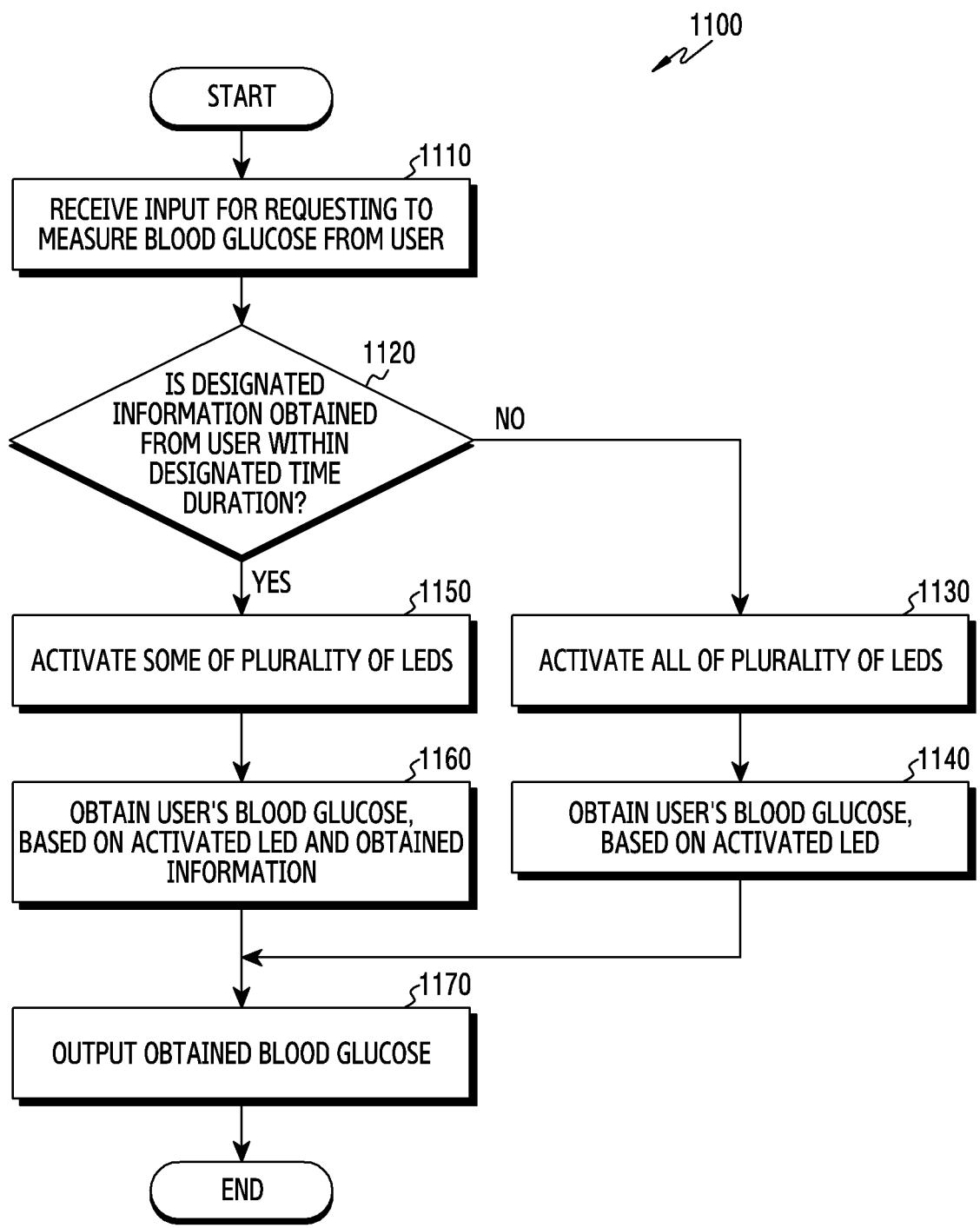
FIG. 11 is a flowchart illustrating an operation of activating at least some of a plurality of LEDs in response to a user input for measuring blood glucose by an electronic device according to an embodiment.

FIG. 11 is a flowchart 1100 illustrating an operation of activating at least some of a plurality of LEDs in response to a user input for measuring blood glucose by an electronic device according to an embodiment. The electronic device of FIG. 11 may correspond to the electronic device 101 of FIG. 1 and FIG. 2. The operation of FIG. 11 may be performed by the electronic device 101 of FIG. 1 and FIG. 2 or the processor 120 of FIG. 1 and FIG. 2. The operation of FIG. 11 may be associated with the operations 1050, 1060, 1070, 1080, and 1090 of FIG. 10.

Referring to FIG. 11, in operation 1110, the electronic device according to an embodiment may receive an input for requesting the measurement of blood glucose from the user. The input may be an operation of touching or clicking a designated visual element (e.g., a button for measuring blood glucose) associated with an application being executed in the electronic device. Alternatively, the input may be an alarm (e.g. an interrupt set at a specific time) configured to initiate the measurement of the blood glucose at a designated time.

Referring to FIG. 11, in operation 1120, the electronic device according to an embodiment may determine whether designated information is obtained from the user within a designated time duration. The designated time duration may be a period of time immediately before when the input is received. That is, one end point of the time duration may correspond to the time when the input is received. In this example, the electronic device may identify the designated information obtained from the user before the input is received. The designated information may include information regarding an optical characteristic of user's skin tissue, such as melanin concentration, oxy-hemoglobin concentration, and/or deoxy-hemoglobin concentration. The designated information may further include the position of the skin tissue (e.g., user's fingertip, left wrist, right wrist, etc.) used to obtain the above mentioned melanin concentration, oxy-hemoglobin concentration, and/or deoxy-hemoglobin concentration.

When the designated information is not obtained from the user within the designated time duration, in operation 1130, the electronic device according to an embodiment may activate all of the plurality of LEDs. The plurality of LEDs to be activated may include a plurality of LEDs that outputs a plurality of wavelengths not overlapping with each other in the visible light wavelength band and an LED that outputs light in the infrared wavelength band.

After activating all of the plurality of LEDs, in operation 1140, the electronic device according to an embodiment may obtain the user's blood glucose based on the activated LEDs. Operations 1130 and 1140 may correspond to operation 340 of FIG. 3 or the operations of FIG. 5. Operations 1130 and 1140 may further be associated with the operations 1070 and 1080 of FIG. 10. The electronic device may identify the user's blood glucose and other information (e.g., concentration of at least one of melanin, oxy-hemoglobin, and deoxy-hemoglobin contained in the skin tissue) required to measure the blood glucose.

When the designated information is obtained from the user within the designated time duration, in operation 1150, the electronic device according to an embodiment may activate some of the plurality of LEDs. For example, the electronic device may activate only the LED that emits light having wavelength greater than or equal to 780 nm. In this example, the electronic device may maintain the deactivation the other LEDs, e.g. the visible-spectrum LEDs.

Referring to FIG. 11, in operation 1160, the electronic device according to an embodiment may obtain user's blood glucose based on an activated LED and the previously obtained information. Thus, the electronic device may compensate for at least one of melanin, oxy-hemoglobin, and deoxy-hemoglobin in the optical density of the reflection light measured by using the activated LED. This may be done based on at least one of the melanin, oxy-hemoglobin, and deoxy-hemoglobin concentrations included in the obtained information. Since the impact on the optical density caused by the melanin concentration, the oxy-hemoglobin concentration, and the deoxy-hemoglobin is compensated for, the electronic device may more accurately measure the concentration of blood glucose from the optical density of the reflection light measured by using the activated LED.

In some embodiments, in the interim between when the designated information was previously obtained and when the input is received in operation 1110, if the electronic device undergoes a state change, the electronic device may exclude part of the designated information while measuring blood glucose in response to the input is received in operation 1110. The state change may include a positional change between the electronic device and a body part or a user's motion state.

For example, the designated information may be previously obtained when the electronic device is worn on the user's right wrist. But if the user moves the electronic device to the left wrist after the designated information is obtained, the melanin concentration may be different on the left wrist than it was on the right wrist. In this case, the electronic device may obtain the user's blood glucose while excluding the previously-obtained melanin concentration information from the measurement. Since the melanin concentration is excluded, the electronic device may obtain a new melanin concentration by activating or operating at least some of the plurality of LEDs, such as the LED corresponding to the blue wavelength band.

In another example, when the user exercises with more than a designated intensity after the designated information is obtained, the electronic device may obtain the user's blood glucose while excluding the previously-obtained oxy-hemoglobin and deoxy-hemoglobin concentrations information from the measurement. Since the oxy-hemoglobin and deoxy-hemoglobin concentrations are excluded, the electronic device may calculate new oxy-hemoglobin and deoxy-hemoglobin concentrations by activating or operating at least some of the plurality of LEDs, such as all of the visible-spectrum LEDs. The electronic device may determine the user's exercise level by using a motion sensor, for example.

Referring to FIG. 11, in operation 1170, the electronic device according to an embodiment may output the obtained or measured blood glucose. The obtained blood glucose may be stored in the electronic device. The obtained blood glucose may be shared with an external electronic device coupled with the electronic device. When the electronic device obtains the blood glucose based on the operations 1130 and 1140, the designated information (e.g., concentrations of melanin, oxy-hemoglobin, and/or deoxy-hemoglobin contained in the skin tissue) used to obtain the blood glucose may be stored in the electronic device or may be shared with the external electronic device.

Figure 12:
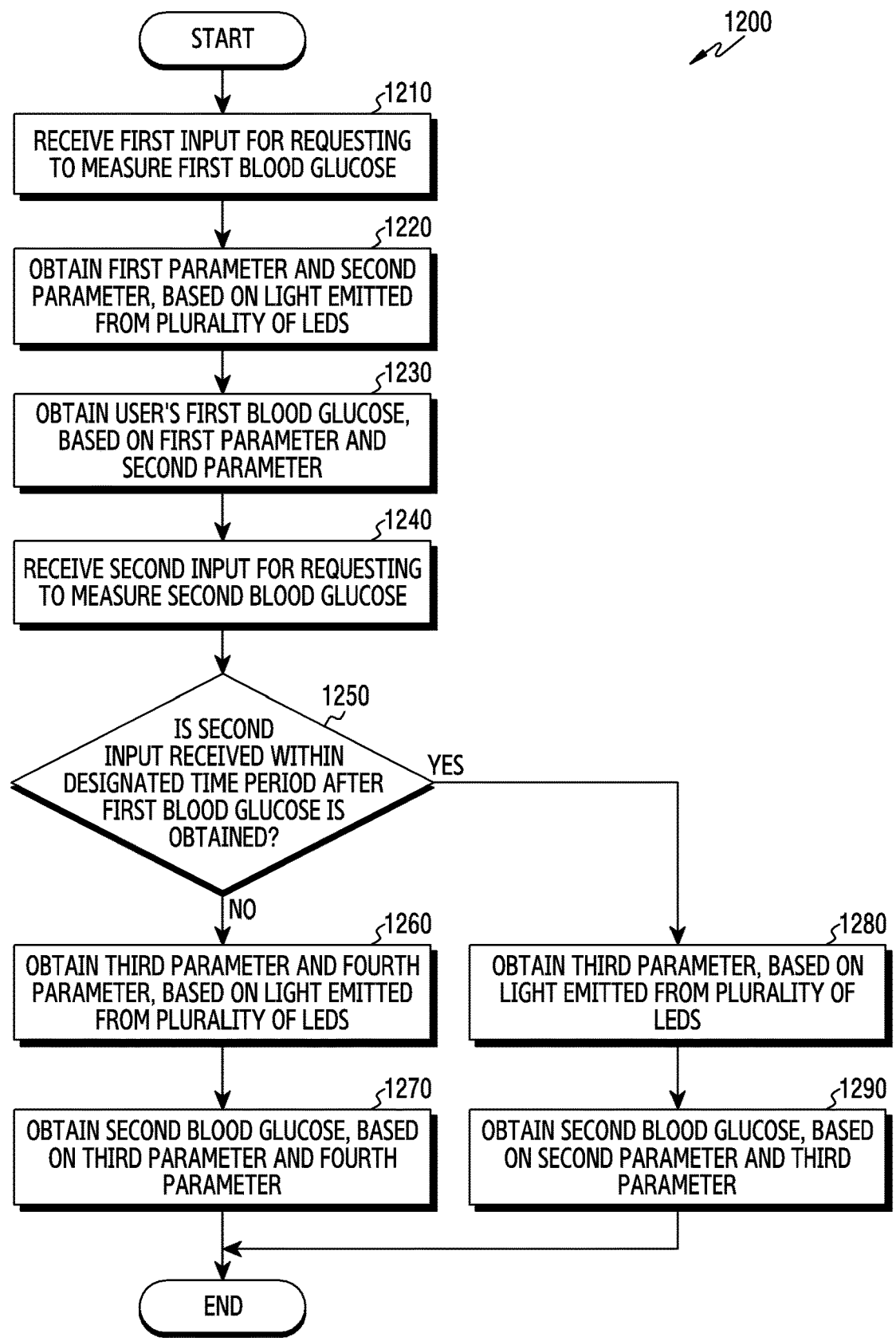
FIG. 12 is a flowchart illustrating an operation of an electronic device according to an embodiment.

FIG. 12 is a flowchart 1200 illustrating an operation of the electronic device 101 according to an embodiment. The electronic device of FIG. 12 may correspond to the electronic device 101 of FIG. 1 and FIG. 2. The operation of FIG. 12 may be performed by the electronic device 101 of FIG. 1 and FIG. 2 or the processor 120 of FIG. 1 and FIG. 2. At least some of the operations of FIG. 12 may similar to some of the operations of FIG. 10.

Referring to FIG. 12, in operation 1210, the electronic device according to an embodiment may receive a first input for requesting the measurement of first blood glucose. The first input may be performed by the user of the electronic device, and may be an operation of touching a designated visual element (e.g., a soft button for measuring blood glucose) in a display, an operation of pressing a designated physical button (e.g., a volume button) of the electronic device, and/or an operation of inputting a voice command into the electronic device. Operation 1210 may be similar to operation 1010 of FIG. 10.

Referring to FIG. 12, in operation 1220, the electronic device according to an embodiment may obtain a first parameter and a second parameter based on light emitted from a plurality of LEDs. The plurality of LEDs may be disposed in a PPG sensor included in the electronic device. The plurality of wavelengths used respectively by the plurality of LEDs may not overlap with each other. For example, wavelengths of the plurality of light beams emitted from the plurality of LEDs may be included in a first wavelength band of between 645 nm and 700 nm, a second wavelength band of between 490 nm and 530 nm, a third wavelength band of between 430 nm and 480 nm, and/or a fourth wavelength band greater than or equal to 700 nm.

The first parameter may include one or more parameters associated with the measurement of the blood glucose. The second parameter may include a parameter associated with the user's skin characteristic. For example, the second parameter may include melanin concentration of the user's skin tissue, concentration of oxy-hemoglobin contained in the user's blood, and/or concentration of deoxy-hemoglobin contained in the blood. The second parameter may include optical densities of light beams corresponding to light beams of the first wavelength to the third wavelength and reflected from the user's skin tissue among the plurality of light beams emitted from the plurality of LEDs. The first parameter may include an optical density of light corresponding to the third wavelength band and/or the fourth wavelength band and reflected from the user's skin tissue among the plurality of light beams emitted from the plurality of LEDs. The first parameter may include the optical density of reflection light in which changes in then optical density caused by the melanin concentration, the oxy-hemoglobin concentration, and/or the deoxy-hemoglobin concentration is compensated for.

The first parameter and/or the second parameter may be stored in a memory of the electronic device. The first parameter and/or the second parameter may be transmitted to an external electronic device coupled with the electronic device via a wireless network or a wired network. The first parameter and/or the second parameter may be maintained for a designated time period in the memory and/or the external electronic device. The designated time period may start from when the first parameter and/or the second parameter are stored in the memory and/or the external electronic device or from when the first user input is received. In an embodiment, in response to another blood glucose measurement request input within the designated time period, the first parameter and/or the second parameter may be used for the additional blood glucose measurement request. In an embodiment, in response to an expiration of the designated time period, the parameters may be deleted.

Referring to FIG. 12, in operation 1230, the electronic device according to an embodiment may obtain user's first blood glucose based on the obtained first parameter and second parameter. The operations 1220 and 1230 may correspond to operation 1020 of FIG. 10. For example, the electronic device may obtain the first blood glucose corresponding to the first input, based on the operation of FIG. 5 or at least one of Equation (3) to Equation (5). In an embodiment, the electronic device may obtain the first blood glucose from the optical density of light included in the fourth wavelength band associated with infrared light and reflected from the user's skin tissue. In an embodiment, the electronic device may obtain the first blood glucose from optical densities of a plurality of light beams included in the fourth wavelength band and the third wavelength band associated with blue color and reflected from the user's skin tissue.

In response to obtaining the first blood glucose, the electronic device may output the obtained blood glucose via a display, a speaker, and/or a communication circuit. The first parameter may include information regarding the obtained first blood glucose. The second parameter may include information regarding the user's skin characteristic.

After the first blood glucose is obtained, in operation 1240, the electronic device according to an embodiment may receive a second input for requesting the measurement of second blood glucose. For example, the user of the electronic device may measure the blood glucose at designated time intervals. Operation 1240 may be similar to operation 1210. In an embodiment, the electronic device may use at least one of the first parameter and second parameter obtained while measuring the first blood glucose in response to the second input received after the first input.

In response to receiving the second input, in operation 1250, the electronic device according to an embodiment may determine whether the second input is received within a designated time period after the first blood glucose is obtained. For example, the electronic device may compare the designated time period and the time difference between when the first input is received and when the second input is received. In another example, the electronic device may compare the designated time period and the time difference between when the first blood glucose is obtained and when the second input is received. As a threshold, the designated time period may be used to determine whether the first parameter or the second parameter can be used to obtain the second blood glucose corresponding to the second input.

When the second input is not received within the designated time period after the first blood glucose is obtained, for example, in operation 1260, the electronic device according to an embodiment may obtain a third parameter and a fourth parameter based on light emitted from the plurality of LEDs. The third parameter may include one or more parameters associated with the measurement of the blood glucose. The fourth parameter may include a parameter associated with the user's skin characteristic. The third parameter and the fourth parameter may respectively correspond to the first parameter and second parameter obtained in the operation 1120, the difference being the third parameter and the fourth parameter were obtained later in time.

Referring to FIG. 12, in operation 1270, the electronic device according to an embodiment may obtain second blood glucose based on the obtained third parameter and fourth parameter. Obtaining of the second blood glucose may be performed similarly to the operation 1230. In response to the second input received after a designated time period has elapsed from when the first blood glucose is obtained, the second blood glucose corresponding to the second input may be obtained based on operations 1260 and 1270 independent of the first blood glucose.

When the second input is received within the designated time period after the first blood glucose is obtained, for example, in operation 1280, the electronic device according to an embodiment may obtain the third parameter based on light emitted from the plurality of LEDs, such as the IR LED or the IR and blue LED. As described above, the third parameter may include one or more parameters associated with the measurement of the blood glucose.

Referring to FIG. 12, in operation 1290, the electronic device according to an embodiment may obtain second blood glucose based on the second parameter associated with the first blood glucose and the obtained third parameter. As the parameter obtained in the operation 1220, the second parameter may include the parameter associated with the user's skin characteristic. In an embodiment, in response to the second input being received within a designated time period after the first blood glucose is obtained, the second blood glucose corresponding to the second input may be obtained with reference to a parameter (e.g., the second parameter) associated with the first blood glucose.

Referring to FIG. 12, the electronic device may reuse, for a second blood glucose, parameter or information previously obtained for a first blood glucose, when blood glucose measurement requests (e.g., the first input and the second input) are continuously received from the user. As a parameter associated with the user's skin characteristic, the parameter that is reused may be associated with the melanin concentration, oxy-hemoglobin concentration, and/or deoxy-hemoglobin concentration. The reusing of the parameter may be performed not only in a single electronic device but also between a plurality of electronic devices.

Figure 13:
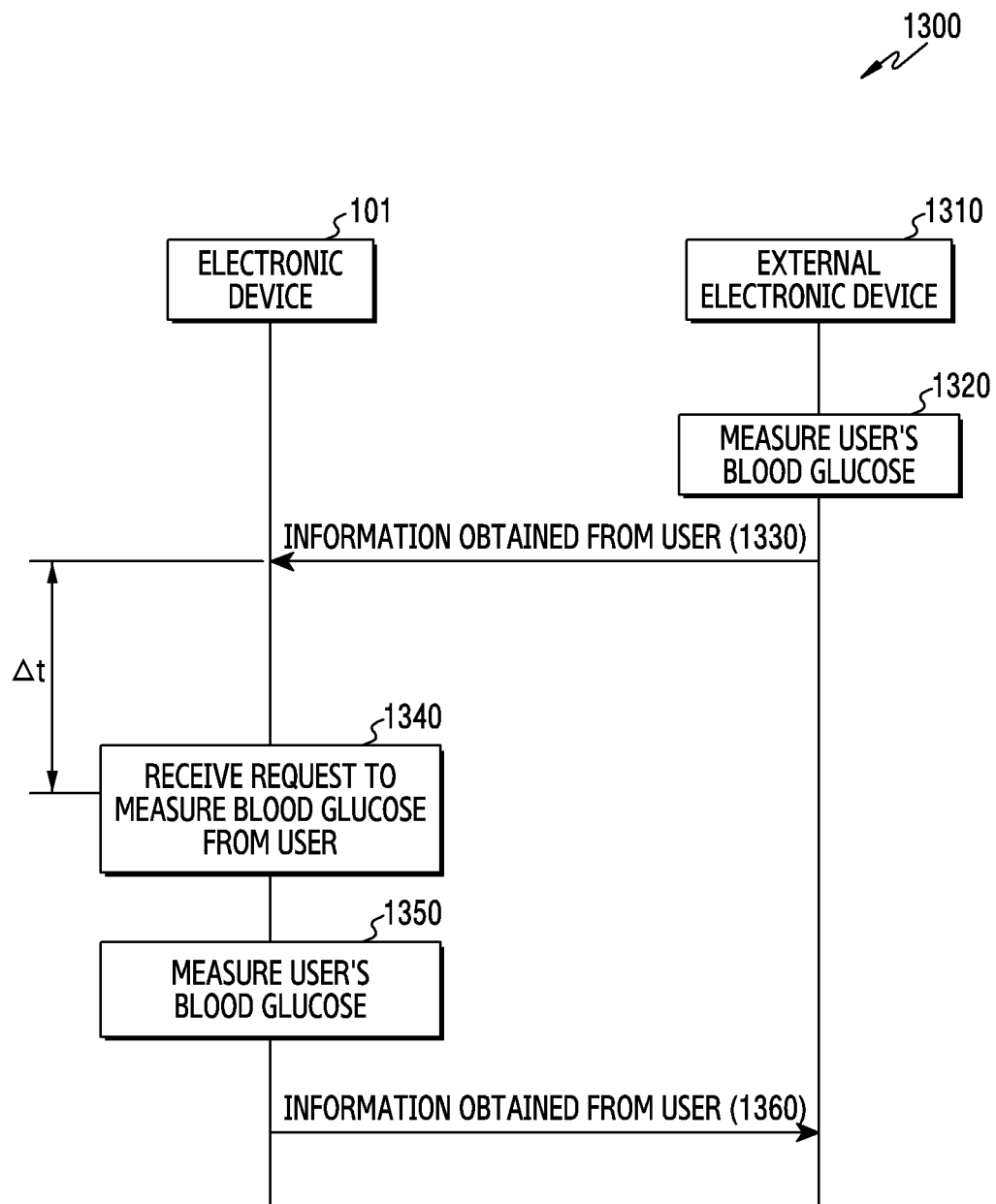
FIG. 13 is a flowchart illustrating an operation of measuring user's blood glucose based on information received by an electronic device from an external electronic device according to an embodiment.

FIG. 13 is a flowchart 1300 illustrating an operation of measuring user's blood glucose based on information received by the electronic device 101 from an external electronic device 1310 according to an embodiment. The electronic device 101 of FIG. 13 may correspond to the electronic device 101-1 of FIG. 4A to FIG. 4C, and the external electronic device 1310 of FIG. 13 may correspond to the electronic device 101-2 of FIG. 6A to FIG. 6D.

Hereinafter, an operation in which the electronic device 101 and the external electronic device 1310 share information regarding blood glucose identified from a user will be described in greater detail with reference to FIG. 13. It is assumed that the electronic device 101 and the external electronic device 1310 identify each other before the operation of FIG. 13 is performed. For example, the electronic device 101 and the external electronic device 1310 may be coupled with each other based on at least one of Near Field Communication (NFC), Bluetooth, and Wireless Fidelity (WiFi). Before the operation of FIG. 13 is performed, the electronic device 101 and the external electronic device 1310 may share information for identifying each other. The information may include whether the electronic device 101 or the external electronic device 1310 is capable or measuring the user's blood glucose and a parameter associated with a body part to be in contact to measure the user's blood glucose.

Referring to FIG. 13, in operation 1320, the external electronic device 1310 according to an embodiment may measure the user's blood glucose. The measurement may be based at least in part on a user request which is input to the external electronic device 1310. The operation 1320 may be performed based at least in part on the operation 340 of FIG. 3 or the operations of FIG. 5. The operation 1320 may be performed based at least in part on the operations 1070 and 1080 of FIG. 10. The operation 1320 may be performed based at least in part on the operations 1130 and 1140 of FIG. 11.

The external electronic device 1310 may measure the user's blood glucose based on a plurality of LEDs which use different wavelengths in visible light and infrared light wavelength bands. After light emitted from the plurality of LEDs is reflected from the user's skin tissue, the external electronic device 1310 may identify the intensity of the reflection light by using at least one PD. The external electronic device 1310 may compare the intensity of light output from the plurality of LEDs and the intensity of reflection light beams reflected from the skin tissue to identify optical densities of the reflection light beams.

The external electronic device 1310 may calculate the user's blood glucose by comparing the optical densities of the respective identified wavelengths. For example, the external electronic device 1310 may calculate a concentration of at least one of melanin, oxy-hemoglobin, and deoxy-hemoglobin contained in the user's skin tissue based on Equation (3) to Equation (6). The external electronic device 1310 may output the calculated blood glucose to the user.

Referring to FIG. 13, in response to calculating the concentration of the user's blood glucose, the external electronic device 1310 may transmit information 1330 obtained from the user to the electronic device 101. The information 1330 may include at least one of the calculated concentration of blood glucose, melanin, oxy-hemoglobin, and deoxy-hemoglobin. The information 1330 may include a parameter associated with when the blood glucose is calculated or when the reflection light is received by the PD to measure the user's blood glucose.

Information transmitted by the external electronic device 1310 may vary depending on the type of the electronic device 101. For example, when the electronic device 101 measures the blood glucose by using another body part distinct from a body part associated with the external electronic device 1310, since the concentration of melanin differs for each body part, the information 1330 may not include the concentration of melanin. For example, when the external electronic device 1310 measures the blood glucose based on a user's fingertip and the electronic device 101 measures the blood glucose based on a user's wrist, since the external electronic device 1310 and the electronic device 101 use different body parts, the external electronic device 1310 may include in the information 1330 parameters other than the parameter for the concentration of melanin.

Referring to FIG. 13, in operation 1340, the electronic device 101 according to an embodiment may receive a request for measuring the blood glucose from the user. The electronic device 101 may identify a time difference $\Delta t$ between when the request is received and when the information 1330 is received. Alternatively, the time difference $\Delta t$ may be between when the request is received and when the external electronic device 1310 measured the blood glucose or when the external electronic device 1301 received reflection light. Information regarding when the external electronic device 1310 measured the blood glucose or when the external electronic device 1301 received reflection light may be included in the information 1330.

In response to receiving the request for measuring the blood glucose from the user in operation 1340, in operation 1350, the electronic device 101 according to an embodiment may measure the user's blood glucose. The electronic device 101 may determine whether the information 1330 will be used in the calculation of the user's blood glucose, based at least in part on the identified time difference $\Delta t$. For example, when the time difference $\Delta t$ is less than a designated time duration, the electronic device 101 may calculate the user's blood glucose by using the information 1330. For example, when the difference between when the request of the operation 1340 is received and when the electronic device 1310 measured the blood glucose is less than the designated time duration, the electronic device 101 may calculate the user's blood glucose by using the information 1330. In another example, when the different between when the request of the operation 1340 is received and when the external electronic device 1310 received the reflection light is less than the designated time duration, the electronic device 101 may calculate the user's blood glucose by using the information 1330. When the identified time difference $\Delta t$ is greater than or equal to the designated time duration, the electronic device 101 may calculate the user's blood glucose without having to use the information 1330.

In an embodiment, among the plurality of LEDs included in the electronic device 101, the type and number of LEDs to be activated in response to the request of the operation 1340 may vary depending on whether the electronic device 101 will use the information 1330 in the calculation of the user's blood glucose. When the electronic device 101 uses the information 1330 in the calculation of the user's blood glucose, only the IR LED may be activated among the plurality of LEDs included in the electronic device 101. When the electronic device 101 uses the information 1330 in the calculation of the user's blood glucose, the electronic device 101 may maintain the deactivation of the visible-spectrum LEDs. When the melanin concentration is not included in the information 1330, the electronic device 101 may activate some of the visible-spectrum LEDs, such as the blue LED. When the electronic device 101 does not use the information 1330 in the calculation of the user's blood glucose, the electronic device 101 may activate all of the plurality of LEDs.

When the electronic device 101 measures the user's blood glucose by using the information 1330, the operation 1350 may be associated at least in part with operations 1050, 1060, and 1080 of FIG. 10 or operations 1140, 1150, and 1160 of FIG. 11 or operations 1250, 1280, and 1290 of FIG. 12. When the electronic device 101 measures the user's blood glucose without having to use the information 1330, the operation 1350 may be performed similarly to the operation 1320. The electronic device 101 may output the measured user's blood glucose to the user.

Referring to FIG. 13, in response to identifying the external electronic device 1310 distinct from the electronic device 101, the electronic device 101 may transmit information 1360 including at least one of the obtained melanin concentration, oxy-hemoglobin concentration, and deoxy-hemoglobin concentration to the external electronic device 1310. The type and number of parameters included in the information 1360 may vary depending on the type of the external electronic device 1310, as described in association with the information 1330.

Figure 14:
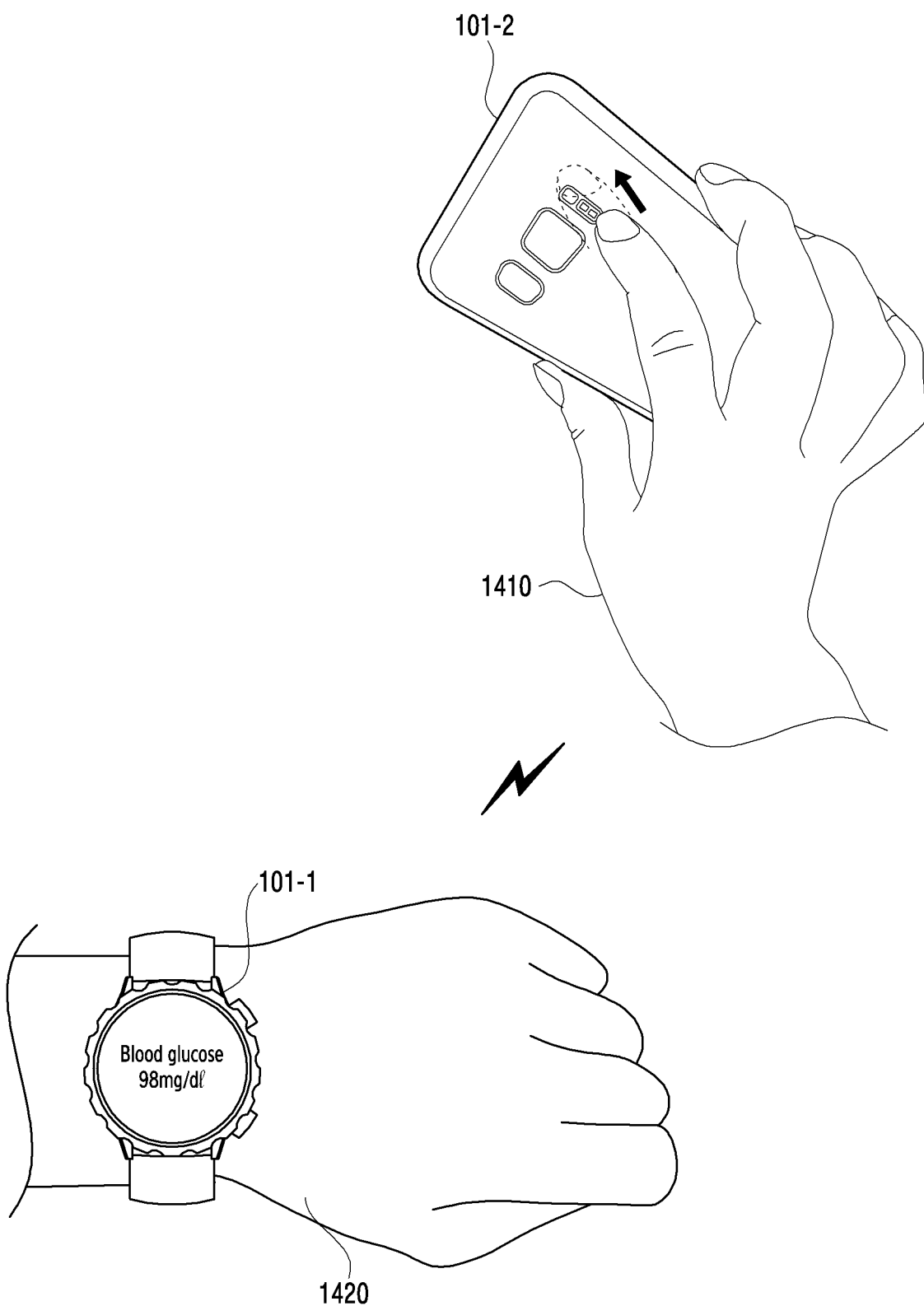
FIG. 14 is a view illustrating an operation in which an electronic device and an external electronic device measure blood glucose based on different body parts of a user, according to an embodiment.

FIG. 14 is a view illustrating an operation in which the electronic device 101-1 and the external electronic device 101-2 measure blood glucose based on different body parts of a user, according to an embodiment. The electronic device 101-1 of FIG. 14 may correspond to the electronic device 101-1 of FIG. 4A to FIG. 4C, and the external electronic device 101-2 of FIG. 14 may correspond to the electronic device 101-2 of FIG. 6A to FIG. 6D. The operation performed by the electronic device 101-1 and external electronic device 101-2 of FIG. 14 may be associated with at least one of the operations described with reference to FIG. 13.

Referring to FIG. 14, the electronic device 101-1 may be a wearable device which can be worn on any one of the wrists of the user. For example, the user may fasten the electronic device 101-1 to a left hand 1420. The electronic device 101-2 may be a smartphone or a tablet. The external electronic device 101-2 may be coupled with the electronic device 101-1 in a wired or wireless fashion.

The electronic device 101-1 and the external electronic device 101-2 may both include a PPG sensor for measuring the blood glucose. For example, the electronic device 101-1 and the external electronic device 101-2 may include the sensor module 176 of FIG. 1 and FIG. 2. In a housing of each of the electronic device 101-1 and the external electronic device 101-2, sensors for measuring blood glucose may be disposed at positions where the sensors can be easily contacted by the user's skin tissue.

The user may request the external electronic device 101-2 to measure the blood glucose. In response to receiving the request for measuring the blood glucose, the external electronic device 101-2 may output a message guiding the user to place a fingertip in contact with the sensor module 176 of the external electronic device 101-2. Referring to FIG. 14, based on the output message, the user may place a fingertip of the right hand 1410 to touch the sensor module of the external electronic device 101-2.

The external electronic device 101-2 may output one or more light beams of different wavelengths towards the fingertip. Based on optical densities of one or more reflection light beams reflected from the fingertip, the external electronic device 101-2 may measure the user's blood glucose. The operation in which the external electronic device 101-2 measures the user's blood glucose may correspond to, for example, the operation 1320 of FIG. 13.

The external electronic device 101-2 may transmit information regarding the measured blood glucose to the electronic device 101-1. The information to be transmitted may include blood glucose value, melanin concentration value, oxy-hemoglobin value, and/or deoxy-hemoglobin value. Since the body part (fingertip) used by the external electronic device 101-2 to measure the blood glucose is different from the body part (e.g. wrist) used by the electronic device 101-1 to measure the blood glucose, the external electronic device 101-2 may transmit the values except for the melanin concentration value to the electronic device 101-1. For example, the external electronic device 101-2 may transmit at least one of the oxy-hemoglobin value and the deoxy-hemoglobin value to the electronic device 101-1.

After the external electronic device 101-2 transmits the information regarding the measured blood glucose to the electronic device 101-1, the user may request the electronic device 101-1 to measure the blood glucose. The electronic device 101-1 may determine whether to use the information received from the external electronic device 101-2, by comparing when the information is received from the external electronic device 101-2 to when the user requests the electronic device 101-1 to measure the blood glucose. The operation in which the electronic device 101-1 determines whether to use the information received from the external electronic device 101-2 by comparing the time points may be associated with the operation 1350 of FIG. 13.

When the electronic device 101-1 determines to use the information received from the external electronic device 101-2, the electronic device 101-1 may operate some of a plurality of LEDs (e.g., the IR LED). Based on the operating LED and the information received from the external electronic device 101-2, the electronic device 101-1 may measure the user's blood glucose. When the electronic device 101-1 determines not to use the information received from the external electronic device 101-2, the electronic device 101-1 may operate all of the plurality of LEDs. The electronic device 101-1 may then measure the user's blood glucose, based on all of the plurality of LEDs.

In an embodiment, the electronic device may include an LED of an infrared wavelength and a plurality of LEDs of a visible light wavelength band. The plurality of LEDs of the visible light wavelength band may operate in different wavelength bands (e.g., red wavelength band, green wavelength band, and blue wavelength band). The plurality of LEDs included in the electronic device may emit a plurality of light beams towards adjacent skin tissue, and the electronic device may include at least one PD for receiving a plurality of light beams reflected from the skin tissue.

The electronic device may obtain concentrations of a plurality of materials contained in the skin tissue, based on intensities of the plurality of light beams to be emitted and intensities of the plurality of reflection light beams received. The plurality of materials may include melanin, oxy-hemoglobin, and deoxy-hemoglobin. Based on how the concentrations of the plurality of materials impact the intensities of the reflection light beams, the electronic device may more accurately measure the concentration of the blood glucose.

Methods based on the embodiments disclosed in the claims and/or specification of the disclosure can be implemented in hardware, software, or a combination of both.

When implemented in software, computer readable recording medium for storing one or more programs (i.e., software modules) can be provided. The one or more programs stored in the computer readable recording medium are configured for execution performed by one or more processors in the electronic device. The one or more programs include instructions for allowing the electronic device to execute the methods based on the embodiments disclosed in the claims and/or specification of the disclosure.

The program (i.e., the software module or software) can be stored in a random access memory, a non-volatile memory including a flash memory, a Read Only Memory (ROM), an Electrically Erasable Programmable Read Only Memory (EEPROM), a magnetic disc storage device, a Compact Disc-ROM (CD-ROM), Digital Versatile Discs (DVDs) or other forms of optical storage devices, and a magnetic cassette. Alternatively, the program can be stored in a memory configured in combination of all or some of these storage media. In addition, the configured memory can be plural in number.

Further, the program can be stored in an attachable storage device capable of accessing the electronic device through a communication network such as the Internet, an Intranet, a Local Area Network (LAN), a Wide LAN (WLAN), or a Storage Area Network (SAN) or a communication network configured by combining the networks. The storage device can have an access to a device for performing an embodiment of the disclosure via an external port. In addition, an additional storage device on a communication network can have an access to the device for performing the embodiment of the disclosure.

In the aforementioned specific embodiments of the disclosure, a component included in the disclosure is expressed in a singular or plural form according to the specific example embodiment proposed herein. However, the singular or plural expression is selected properly for a situation proposed for the convenience of explanation, and thus the disclosure is not limited to a single or a plurality of components. Therefore, a component expressed in a plural form can also be expressed in a singular form, or vice versa.

Certain of the above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

While the disclosure has been shown and described with reference to certain preferred embodiments thereof, it will be understood by those skilled in the art that various changes in form and details may be made therein without departing from the spirit and scope of the disclosure as defined by the appended claims. Therefore, the scope of the disclosure is defined not by the detailed description thereof but by the appended claims, and all differences within equivalents of the scope will be construed as being included in the disclosure.

What is claimed is:

1. An electronic device comprising:
   a housing;
   a PhotoPlethysmoGram (PPG) sensor disposed inside the housing, wherein the PPG sensor includes:
   a first Light Emitting Diode (LED) configured to generate light in a first wavelength band,
   a second LED configured to generate light in a second wavelength band,
   a third LED configured to generate light in a third wavelength band,
   a fourth LED configured to generate light in a fourth wavelength band, and
   a light receiving module including at least one photo diode;
   a processor operatively coupled with the PPG sensor; and
   a memory operatively coupled with the processor, wherein the memory includes instructions that, when executed, cause the processor to:
   in response to an input requesting metering of blood glucose, determine whether predesignated biometric information was obtained from a user within a predesignated time range prior to a present time;
   based on the determination, execute one of:
      activating LEDs as to include all of the first to fourth LEDs, or
      activating LEDs as to omit a subset of the first to fourth LEDs less than an entirety of the first to fourth LEDs;
   measure optical densities of light generated by the activated LEDs; and
   calculate a blood glucose value of the user based at least in part on the measured optical densities.

2. The electronic device of claim 1, wherein the omitted subset of the first to fourth LEDs are utilized to meter the predesignated biometric information.

3. The electronic device of claim 2, wherein the instructions further cause the processor to:
   when predesignated biometric information was obtained within the predesignated time range, activate a part of the first to fourth LEDs excluding the subset, and calculate the blood glucose value using the part of the first to fourth LEDs and the predesignated biometric information; and
   when predesignated biometric information was not obtained within the predesignated time range, activate all of the first to fourth LEDs, and calculate the blood glucose value using all of the first to fourth LEDs.

4. The electronic device of claim 1, wherein
   the predesignated biometric information is obtained from the user within the predesignated time range and is stored in the memory before the input is received.

5. The electronic device of claim 1, wherein the predesignated biometric information includes at least one of a melanin concentration of the user's skin, an oxy-hemoglobin concentration of the user's blood glucose, or a deoxy-hemoglobin concentration.

6. The electronic device of claim 1,
   wherein the first wavelength band is between 645 nm and 700 nm,
   wherein the second wavelength band is between 490 nm and 530 nm,
   wherein the third wavelength band is between 430 nm and 480 nm, and
   wherein the fourth wavelength band is greater than or equal to 780 nm.

7. The electronic device of claim 1, wherein, to calculate the blood glucose value, the instructions further cause the processor to:
   measure the optical densities using a plurality of photo diodes included in the PPG sensor, the plurality of photo diodes including the at least one photo diode; and
   respectively apply a plurality of weights corresponding to the plurality of photo diodes to the measured optical densities.

8. The electronic device of claim 7, wherein each of the plurality of weights is associated with a distance from a corresponding photo diode in the plurality of photo diodes to the first LED, the second LED, the third LED, and the fourth LED.

9. The electronic device of claim 1, wherein the PPG sensor is exposed through a part of the housing which can be in contact with at least part of the user's body.

10. The electronic device of claim 1, further comprising a communication circuit configured to be communicatively coupled with an external electronic device,
wherein
the predesignated biometric information is obtained from the user within the predesignated time range in response to a user input received by the external electronic device, before in response to receiving the input.

11. A method in an electronic device including a plurality of light emitting diodes (LED) for emitting light at respectively different wavelengths, comprising:
in response to detecting, via input circuitry, a request to meter blood glucose, determining, by a processor, whether predesignated biometric information is obtained from a user within a predesignated time range prior to a present time;
based on the determination, executing one of:
activating LEDs as to include all of the plurality of LEDs, or
activating LEDs as to omit a subset of the plurality of LEDs from activation, less than an entirety of the plurality of LEDs;
measuring optical densities of light generated by the activated LEDs; and
calculating a blood glucose value of the user based at least in part on the measured optical densities.

12. The method of claim 11, wherein the omitted subset of the plurality of LEDs are utilized to meter the predesignated biometric information.

13. The method of claim 12, wherein, when predesignated biometric information is obtained within the predesignated time range, a part of the first to fourth LEDs excluding the subset is activated, and the blood glucose value is calculated using the part of the first to fourth LEDs and the predesignated biometric information; and
when predesignated biometric information is not obtained within the predesignated time range, all of the first to fourth LEDs are activated, and the blood glucose value is calculated using all of the first to fourth LEDs.

14. The method of claim 11, further comprising:
obtaining the predesignated biometric information from the user within the predesignated time range; and
storing the predesignated biometric information in the memory before the input is received.

15. The method of claim 11, wherein the predesignated biometric information includes at least one of a melanin concentration of skin, an oxy-hemoglobin concentration of the blood glucose, or a deoxy-hemoglobin concentration.

16. The method of claim 11, wherein the plurality of LEDs includes:
a first LED having a first wavelength band between 645 nm and 700 nm,
a second LED having a second wavelength band between 490 nm and 530 nm,
a third LED having a third wavelength band between 430 nm and 480 nm, and
a fourth LED having a fourth wavelength band greater than or equal to 780 nm.

17. The method of claim 11, wherein, to calculate the blood glucose value, the method further comprising:
measuring the optical densities using a plurality of photo diodes included in a PPG sensor, the plurality of photo diodes including at least one photo diode; and
respectively applying a plurality of weights corresponding to the plurality of photo diodes to the measured optical densities.

18. The method of claim 17, wherein each of the plurality of weights is associated with a distance from a corresponding photo diode in the plurality of photo diodes to a first LED, a second LED, a third LED, and a fourth LED.

19. The method of claim 11, wherein a PPG sensor is exposed through a part of a housing of the electronic device, and configured to contact with at least part of the user's body.

20. The method of claim 11, further comprising:
obtaining the predesignated biometric information from the user within the predesignated time range in response to a user input received by an external electronic device, before receiving the input.

* * * * *

UNITED STATES PATENT AND TRADEMARK OFFICE
CERTIFICATE OF CORRECTION

| | |
|---|---|
| PATENT NO. | : 11,497,453 B2 |
| APPLICATION NO. | : 16/689258 |
| DATED | : November 15, 2022 |
| INVENTOR(S) | : Hyejung Seo et al. |

It is certified that error appears in the above-identified patent and that said Letters Patent is hereby corrected as shown below:

In the Claims

Column 39, Claim 10, Line 11 should read as follows:
--…before receiving the input…--

Signed and Sealed this
Thirteenth Day of December, 2022

Katherine Kelly Vidal
*Director of the United States Patent and Trademark Office*